(12) United States Patent
Hiller et al.

(10) Patent No.: US 10,150,114 B2
(45) Date of Patent: Dec. 11, 2018

(54) TEST ELEMENTS FOR DETECTING AT LEAST ONE ANALYTE IN A BODY FLUID, AS WELL AS METHODS OF MANUFACTURING THE SAME

(71) Applicant: Roche Diabetes Care, Inc., Indianapolis, IN (US)

(72) Inventors: Bernd Hiller, Lampertheim (DE); Rudolf Pachl, Ellerstadt (DE); Daniela Pfiffi, Mannheim (DE); Ewald Rieger, Bobenheim-Roxheim (DE); Christa Sternberger, Hockenheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 16/014,034

(22) Filed: Jun. 21, 2018

(65) Prior Publication Data

US 2018/0297030 A1 Oct. 18, 2018

Related U.S. Application Data

(60) Division of application No. 14/961,211, filed on Dec. 7, 2015, now Pat. No. 10,029,252, which is a
(Continued)

(30) Foreign Application Priority Data

Jun. 7, 2013 (EP) .................................... 13170989

(51) Int. Cl.
*B01L 3/00* (2006.01)
*G01N 21/77* (2006.01)
(Continued)

(52) U.S. Cl.
CPC .......... *B01L 3/502707* (2013.01); *C12Q 1/54* (2013.01); *G01N 21/77* (2013.01);
(Continued)

(58) Field of Classification Search
CPC ....... B01L 3/502707; B01L 2400/0406; B01L 2300/161; B01L 2300/041; B01L 2200/12;
(Continued)

(56) References Cited

U.S. PATENT DOCUMENTS 5,759,364 A 6/1998 Charlton et al.
6,592,815 B1 7/2003 Zimmer
(Continued)

FOREIGN PATENT DOCUMENTS

DE 19753849 A1 6/1999
EP 1035920 B1 7/2002
(Continued)

OTHER PUBLICATIONS

Dispercoll® U Polyurethane Dispersions, www.bayermaterialsciencenafta.com/products, Jan. 23, 2013, pp. 1-4.
(Continued)

*Primary Examiner* — Dennis White

(57) ABSTRACT

Methods are disclosed for manufacture of test elements for detecting at least one analyte in a body fluid, where the test elements include a housing having at least one base element and at least one cover element. The methods include providing the base element, and mounting the cover element to the base element with an adhesive, wherein the adhesive contacts at least one test field of the cover element such that the adhesive is interposed between the test field and the base element and at least partially covers the test field. The test elements also include at least one fluid channel formed within the housing, where the the fluid channel includes a capillary region and a measurement region. The capillary region and the measurement region have differing aspect ratios. The at least one test field has at least one test chemical, where the test chemical is adapted to change at
(Continued)

least one optically measurable property in the presence of the analyte.

19 Claims, 5 Drawing Sheets

Related U.S. Application Data continuation of application No. PCT/EP2014/061832, filed on Jun. 6, 2014.

(51) Int. Cl.
*G01N 33/543* (2006.01)
*C12Q 1/54* (2006.01)

(52) U.S. Cl.
CPC .... *G01N 33/54386* (2013.01); *B01L 2200/12* (2013.01); *B01L 2300/041* (2013.01); *B01L 2300/161* (2013.01); *B01L 2400/0406* (2013.01); *G01N 2021/7766* (2013.01); *G01N 2021/7796* (2013.01)

(58) Field of Classification Search
CPC .... C12Q 1/54; G01N 33/54386; G01N 21/77; G01N 2021/7766; G01N 2021/7796
See application file for complete search history.

(56) References Cited

U.S. PATENT DOCUMENTS

| | | |
|---|---|---|
| 7,008,799 B1 | 3/2006 | Zimmer et al. |
| 7,238,534 B1 | 7/2007 | Zimmer |
| 8,809,013 B2 | 8/2014 | Heindl et al. |
| 9,173,608 B2 | 11/2015 | Kuhr et al. |
| 2007/0278097 A1 | 12/2007 | Bhullar et al. |
| 2012/0063970 A1 | 3/2012 | List et al. |

FOREIGN PATENT DOCUMENTS

| | | |
|---|---|---|
| EP | 1385002 B1 | 9/2007 |
| EP | 1482299 B1 | 9/2010 |
| WO | 9929429 A1 | 6/1999 |
| WO | 9930158 A1 | 6/1999 |
| WO | 2004086970 A1 | 10/2004 |
| WO | 2005114160 A1 | 12/2005 |
| WO | 2007012494 B1 | 3/2007 |
| WO | 2007118647 A1 | 10/2007 |
| WO | 2010094426 A1 | 8/2010 |
| WO | 2010094427 A2 | 8/2010 |
| WO | WO-2013024030 A1 * | 2/2013 ........ B01L 3/502746 |

OTHER PUBLICATIONS

Hoenes, Joachim et al., The Technology Behind Glucose Meters: Test Strips, Diabetes Technology & Therapeutics, 2008, pp. S-10-S-26, vol. 10, Supplement 1.

Von Ketteler, Alexa et al., Fluorescence Properties of Carba Nicotinamide Adenine Dinucleotide for Glucose Sensing, ChemPhysChem, 2012, pp. 1302-1306, vol. 13.

* cited by examiner (B-B)

(D)

TEST ELEMENTS FOR DETECTING AT LEAST ONE ANALYTE IN A BODY FLUID, AS WELL AS METHODS OF MANUFACTURING THE SAME

CROSS-REFERENCE TO RELATED APPLICATIONS

This patent application is a divisional of U.S. patent application Ser. No. 14/961,211 filed Dec. 7, 2015, which claims priority to International Application No. PCT/EP2014/061832 (filed 6 Jun. 2014), which claims priority to and the benefit of EP Patent Application No. 013170989.1 (filed 7 Jun. 2013). Each patent application is incorporated herein by reference as if set forth in its entirety.

TECHNICAL FIELD

This disclosure relates generally to chemistry and medical diagnostics, and more particularly, it relates to test elements for detecting at least one analyte in a body fluid, as well as to methods of manufacturing the same.

BACKGROUND

A large number of devices and methods are known for determining a presence and/or concentration of one or more analytes in body fluids. Without restricting the scope of this disclosure, in the following, reference is made mainly to determining glucose concentrations, particularly in body fluids such as whole blood and/or interstitial fluid. However, other applications and analytes are feasible.

For performing fast and simple measurements, several types of test elements are known, which use one or more test chemicals. The test chemical (also referred to as the test substance, the test chemistry, the test reagent or the detector substance) typically is a chemical compound or a mixture of chemical compounds adapted for performing a detection reaction for an analyte of interest. For details of potential test chemicals and test elements incorporating such test chemicals, which may be used herein, reference may be made to Hones et al. (2008) *Diabetes Technol. Ther.* 10:S10-S26. Other types of test elements and/or test substances are feasible and may be used herein.

By using one or more test chemicals, a detection reaction may be initiated, the course of which depends on the concentration of the analyte of interest. Typically, as may also be the case in, the test chemical is adapted to perform at least one detection reaction when the analyte is present in the body fluid, where the extent and/or the degree of the detection reaction depends on the analyte concentration. Generally, the test chemical may be adapted to perform a detection reaction in the presence of the analyte, where at least one detectable property of at least one of the body fluid and the test chemical is changed due to the detection reaction. The at least one detectable property generally may be a physical property or a chemical property.

In the following, reference will be made to optical detection reactions (i.e., optical test chemicals being adapted to change at least one optically measurable property in the presence of the analyte). The at least one optically detectable property generally may be detected by detecting light propagating from the test chemical to a detector. This light, which may be referred to as the detection light, may be light emitted by the test chemical itself and/or may be light that is scattered and/or reflected by the test chemical. Thus, the light may be luminescence light, such as fluorescence light, the generation of which may be excited by primary light, such as excitation light, illuminating the test chemical. Additionally or alternatively, the light may be light that is reflected by the test chemical, such as by reflecting and/or scattering primary light. In the latter case, the test chemical may be adapted to change at least one reflective property due to the detection reaction, such as a color.

In the art, many types of test elements including at least one test chemical are known. In many cases, the test elements are in the form of test strips having at least one capillary element for transporting the body fluid from at least one application position, such as from at least one application opening, to one or more test fields including the at least one test chemical.

For example, EP Patent No. 1 482 299 discloses an optical-based test element for use in determining an analyte in a liquid sample. The test element includes a base having a capillary channel formed in a surface of the base, the capillary channel being adapted to move a liquid sample from an inlet to a reaction area formed in the base. The test element further includes a polymer carrier having a lower surface adhered to the surface of the base. The polymer carrier is disposed over at least a portion of the capillary channel. Further, the test element includes a test membrane adhered to the lower surface of the polymer carrier, where the test membrane contains a reagent. The test membrane also extends from the polymer carrier into the reaction area such that the test membrane is arranged to allow the flow of the liquid sample across a bottom surface and an edge of the test membrane.

U.S. Pat. No. 5,759,364 discloses an electrochemical test element that is made up of an insulating base plate bearing an electrode on its surface that reacts with an analyte to produce mobile electrons. The base plate is mated with a lid of a deformable material, which has a concave area surrounded by a flat surface so that when mated to the base plate there is formed a capillary space into which a liquid sample can be drawn. The side of the lid facing the base is coated with a polymeric material that serves to bond the lid to the base plate and to increase the hydrophilic nature of the capillary space.

US Patent Application Publication No. 2007/0278097 discloses a test element including a base substrate on which an electrode system is formed. One or more laminate layers overlie the base substrate to form a sample receiving chamber in which a reagent is deposited. An opening is provided from the sample receiving chamber to the exterior of the test element. The layers and the base substrate are laser welded to secure the test element. One of the layer and base substrate is light-transmissive to allow laser welding at the interface there between. The test element may be formed from a series of continuous webs that are subsequently sliced to form individual test elements.

Intl Patent Application Publication No. WO 2005/114160 discloses a method of manufacturing a diagnostic test element. Therein, an application sheet is provided, having a plurality of adhesive dots thereon. Further, a first substrate layer is provided having at least one feature located thereon, and, further, a second substrate layer is provided. At least one of the plurality of adhesive dots located on the application sheet is transferred to the first substrate layer, and the first substrate layer is aligned with the second substrate layer and is attached to the second substrate layer, using the transferred adhesive dots. The attaching of the first and second substrate layers is performed without any additional alignment.

Intl Patent Application Publication No. WO 2004/086970 discloses a method of producing combined puncturing and measuring devices for detecting an analyte in a liquid sample. The combined puncturing and measuring devices include a support and a detection element. Recesses that define puncturing points are formed on a surface of a band-shaped support material. A detection element is applied to the band-shaped support material. Individual puncturing/measuring disposable bodies are separated either singly or in groups from the band-shaped support material at a separating line.

Intl Patent Application Publication No. WO 99/30158 discloses an analytic test element for determining an analyte in a liquid sample. The test element includes a detection element and a canal that permits capillary liquid transport, where the canal has a test sample feeding opening situated on one end of the canal that permits capillary liquid transport. The canal steadily tapers from the sample feeding opening in a direction of the capillary transport to at least the beginning of the detection element. Herein, the detection element may be inserted in a matching recess integrated into an element that covers the analytic test element.

EP Patent Application Publication No. 1 035 920 discloses a device for collecting liquid samples for analytic test elements in which the liquid sample is transported from a sampling location to a determination location via a capillary active canal. The capillary active canal is essentially produced by a carrier, a covering, and an optional intermediate layer that lies between the covering and the support, whereby a recess is located in an area, the area constructing the canal permitting capillary liquid transport.

Intl Patent Application Publication No. WO 99/29429 discloses an analytic test element for determining an analyte in a liquid sample. The test element includes an inert carrier, a detection element, and a canal that permits capillary liquid transport. The canal has a liquid sample feeding opening situated on one end of the canal that permits capillary liquid transport and has a vent opening on the other end of the canal. The canal is at least partially constructed by the carrier and the detection element and extends at least to the edge of the detection element, the edge being adjacent to the vent opening, in a direction of the capillary transport.

EP Patent Application Publication No. 1 385 002 discloses a disposable test element having a bonded structure forming channels and a reaction/measurement chamber being positioned over the sensitive surfaces that takes defined liquid sample volumes. As a flat sensor or test strip, the test element has a compartment structure, a sample holding channel with a surfactant on its inner surface or a porous hydrophilic filling and an inflow opening, a reaction/measurement chamber where the mean cross section is at least twice as deep and/or wide as the sample channel, and an enzyme or enzyme system that recognizes the analyte, together with an electron mediator. A sample stop channel with hydrophobic surface coating or a porous filling material has a mean cross section that is at least half as deep and/or wide as the outlet opening from the reaction/measurement chamber. The sample collector zone has a large volume capacity with a mean cross section at least twice as deep and/or wide as the stop channel. The channels and chamber are all interconnected. The structure is irreversibly bonded to the test element so that the reaction/measurement chamber is placed over the sensitive surfaces of the test element.

Despite the advantages implied by the above-mentioned, known devices and methods, a large number of technical challenges remain, specifically regarding designing and manufacturing of test elements, especially optical test elements. Thus, for optical test elements, a uniform test field having a large area and a uniform wetting of the test field is a challenge, as opposed to electrochemical test elements.

Further, manufacturing of capillary elements, specifically at mass manufacturing scale, still is a challenge. This is because a precise positioning of the elements forming the capillary, such as a base foil, a cover foil and spacer elements forming the walls of the capillary, is required. Further, to reduce the liquid sample amount required for a single test, the volume of the capillary has to be reduced. On the other hand, a reliable wetting of the test field and short filling times of the capillary have to be guaranteed. For this purpose, hydrophilic materials such as hydrophilic cover foils are used that are expensive and, thus, contravene the overall desire to keep costs at a low level. Further, by using common processes for manufacturing the test elements, the overall geometry of the capillary structure of the test element imposes tight limits to the design of the test elements, specifically due to the cutting processes that are used for forming the capillaries.

For the foregoing reasons, there is a need for test elements and methods of manufacturing the same that at least partially avoid the above-mentioned problems and challenges of known devices and methods. Specifically, test elements and methods are provided, which, on the one hand, are highly reliable, require small sample volumes and achieve short testing times. Moreover, and on the other hand, manufacturing costs and effort for manufacturing are kept at a low level or even reduced when compared to known manufacturing methods, specifically with regard to a simplification of method steps and positioning steps.

BRIEF SUMMARY

An inventive concept disclosed herein includes individually adapting the aspect ratios of the capillary region and the measurement region to provide highly reliable test elements that require small sample volumes and achieve short testing times. This inventive concept is achieved by providing at least one fluid channel having a capillary region and a measurement region, where the capillary region and the measurement region each have a different aspect ratio. This inventive concept can be incorporated into exemplary test elements and methods of manufacture as described herein and in more detail below.

For example, test elements are provided that include a housing having at least one base element and at least one cover element. The test element also includes at least one fluid channel formed within the housing, where the at least one fluid channel includes a capillary region and a measurement region, and where the capillary region and the measurement region each have a different aspect ratio. The cover element includes at least one test field having at least one test chemical, where the at least one test chemical changes at least one optically measurable property in the presence of an analyte of interest, and where the cover element is mounted to the base element by using at least one adhesive, the adhesive contacting the at least one test field.

In some instances, the fluid channel has at least two sections/regions having differing depths. In other instances, the capillary region has a first depth and the measurement region has a second depth, the first depth being different from the second depth. In certain instances, the first depth is about 50 μm to about 300 μm, about 100 μm to about 200 μm, or even about 140 μm to about 150 μm; and the second depth is about 20 μm to about 150 μm, about 30 μm to about 100 μm, or even about 70 μm. Alternatively, the first depth is larger than the second depth and exceeds the second depth by a factor of about 1.3 to about 3, by a factor of about 1.5 to about 2.5, or even by a factor of about 2.

In some instances, the capillary region has a uniform depth. In other instances, the measurement region has a uniform depth.

In some instances, the fluid channel includes a transition region in between the capillary region and the measurement region. In some instances, a depth of the fluid channel steadily changes in the transition region. In other instances, the depth steadily decreases from the capillary region to the measurement region. In still other instances, the depth of the fluid channel forms a ramp in the transition region.

In some instances, the capillary region has an aspect ratio of about 0.1 to about 1.5, of about 0.2 to about 1.0, or even of about 0.3 to about 0.4, where the aspect ratio of the capillary region is defined by a maximum depth of the capillary region, divided by a maximum width of the capillary region. In some instances, the measurement region has an aspect ratio of about 0.005 to about 0.2, of about 0.01 to about 0.1, of about 0.02 to about 0.06, or even of about 0.04, where the aspect ratio of the measurement region is defined by a maximum depth of the capillary region, divided by a maximum width of the measurement region. In other instances, the capillary region has an aspect ratio that exceeds the measurement region aspect ratio by a factor of about 2 to about 20, by a factor of about 5 to about 15, or even by a factor of about 9 to about 10.

In some instances, the fluid channel, in the capillary region, has a maximum width of about 100 µm to about 1.0 mm, a maximum width of about 200 µm to about 800 µm, or even a maximum width of about 300 µm to about 500 µm. In other instances, the fluid channel, in the measurement region, has a maximum width of about 500 µm to about 2.5 mm, a maximum width of about 1.0 mm to about 2.0 mm, or even a maximum width of about 1.6 mm to about 1.8 mm.

In some instances, the fluid channel, in the capillary region, has a cross-sectional shape selected from a trapezoidal shape with the longer side of the trapezoid facing towards the cover element, a U-shape, and a V-shape.

In view of the foregoing, methods are provided for manufacturing the test elements disclosed herein. The methods can include providing a test element including a housing having at least one base element and at least one cover element, where the test element further includes at least one fluid channel formed within the housing, where the fluid channel includes a capillary region and a measurement region each having differing aspect ratios, where the cover element includes at least one test field having at least one test chemical, the test chemical changing at least one optically measurable property in the presence of the analyte, and where the method includes the steps of:

a) providing the base element; and
b) mounting the cover element to the base element by using at least one adhesive, where the adhesive contacts the test field of the cover element.

In some instances, step a) includes the following substeps:

a1) providing a carrier foil for the base element; and
a2) providing at least a part of the fluid channel within the carrier foil by using at least one forming process.

The forming process can be a thermoforming process, a stamping, a thermal stamping, a punching, or an embossing. In some instances, the forming process implies a mechanical shaping of the carrier foil, for example, forming at least one opening within the carrier foil such as at least one positioning hole.

In some instances, step b) includes the following substeps:

b1) applying the adhesive to the base element or the cover element or both; and
b2) pressing the cover element to the base element, where substep b2) can be a lamination process.

In the methods, the adhesive can be a thermally activatable adhesive having at least a non-adhesive state, where the thermally activatable adhesive is activatable by thermal activation, thereby bringing the thermally activatable adhesive in an adhesive state. In some instances, especially after performing substep b1), the thermally activatable adhesive is in the non-adhesive state, where, before or during substep b2), the adhesive is thermally activated. In general, the adhesive can be applied by using a coating technique selected from doctor blading, roller coating, printing, spraying, and slot coating.

In the methods, the cover element can include a cover foil covering the capillary region and a test film including the test field, where the test film covers the measurement region, and where step b) includes mounting both the cover foil and the test film to the base element by using the adhesive. In some instances, the cover foil and the test film are arranged according to one of the following ways: (1) the cover foil and the test film are arranged in an adjoining fashion next to each other on top of the base element; or (2) the cover foil at least partially overlaps the test film.

In the methods, the steps can be performed as a reel-to-reel-process. In some instances, a plurality of cover elements and a plurality of base elements is provided by independent continuous webs.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIG. 3B shows a cross-sectional view of the carrier foil 122 along cutting line B-B in FIG. 3A; FIG. 3C shows an enlarged view of region D in FIG. 3B; FIG. 3D shows a longitudinal cross-section along the z-axis along cutting line E-E in FIG. 3A in two different magnifications (10:1 and 40:1); FIG. 3E shows a cross-sectional view along cutting line A-A in FIG. 3A; and FIG. 3F shows an enlarged view of region C in FIG. 3E.

Corresponding reference characters indicate corresponding parts throughout the several views of the drawings.

Figure 1:
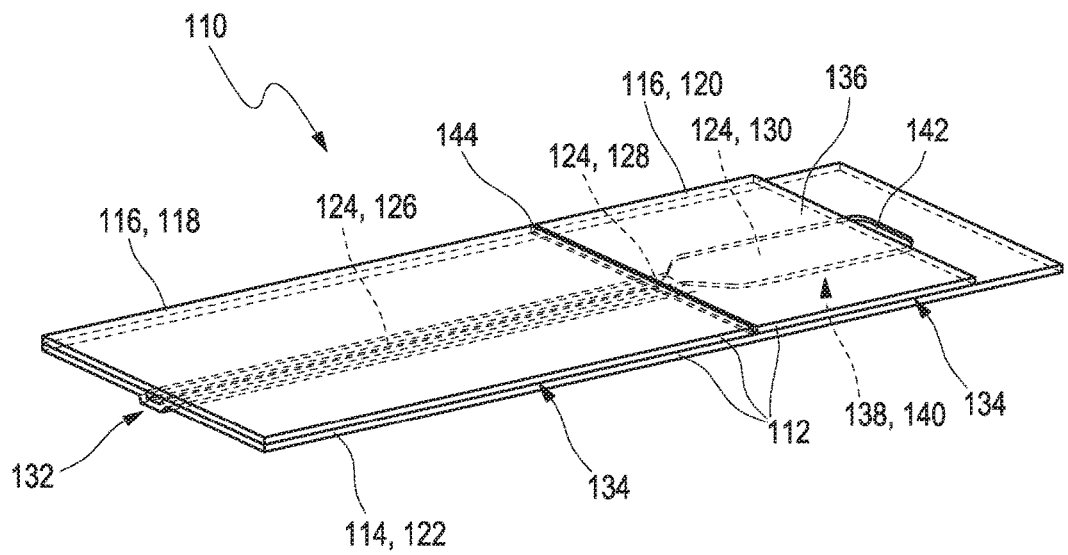
FIG. 1 shows a perspective view of an exemplary test element.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The test elements and methods now will be described more fully hereinafter with reference to the accompanying drawings, in which some, but not all embodiments of the inventive concept are shown. Indeed, the test elements and methods may be embodied in many different forms and should not be construed as limited to the embodiments set forth herein; rather, these embodiments are provided so that this disclosure will satisfy applicable legal requirements.

Likewise, many modifications and other embodiments of the test elements and methods described herein will come to mind to one of skill in the art to which the disclosure pertains having the benefit of the teachings presented in the foregoing descriptions and the associated drawings. Therefore, it is to be understood that the test elements and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the test elements and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

Test elements are disclosed herein that include a housing having at least one base element and at least one cover element. The test elements also include at least one fluid channel formed within the housing, where the fluid channel has a capillary region and a measurement region. The capillary region and the measurement region have differing aspect ratios. The at least one cover element includes at least one test field having at least one test chemical, where the test chemical is adapted to change at least one optically measurable property in the presence of the analyte.

As used herein, "test element" means an arbitrary element adapted for qualitatively and/or quantitatively detecting at least one analyte in a body fluid. In some instances, the test element is a test strip including one or more test fields; however, other embodiments are feasible, such as band-shaped test elements.

With regard to potential analytes to be detected and/or with regard to potential body fluids to be used, reference may be made to the discussion of the prior art given above. In some instances, the test elements herein are adapted for detecting glucose in blood and/or interstitial fluid. It shall be noted, however, that other types of analytes and/or other types of body fluids may be used alternatively or additionally.

It shall be noted that the test elements described herein may be manufactured by methods described herein. In turn, the methods of manufacturing described herein may be used for manufacturing the test element described herein. Thus, with regard to optional embodiments of the test elements, reference may be made to the methods, and vice versa. However, other embodiments are feasible.

The test elements and methods of manufacture thereof that are disclosed herein imply a large number of advantages. With regard to the possibility of providing structures having different aspect ratios, a high flexibility with regard to filling times of the fluid channel and/or parts thereof is given. For example, filling times may be optimized by using an appropriate geometry of the fluid channel, as will be outlined with respect to exemplary embodiments given in further detail below. Specifically for optical test elements, filling times and uniform filling of the fluid channel may form an important aspect of reliability, significant advantages specifically for optical test elements may occur. Specifically, a uniform wetting of the test field and/or of a test area of the test field (such as an area of the test field accessible to the body fluid) may be achieved, which is essential for reliable optical measurements. Still, by providing the possibility of individually adapting the aspect ratios of the capillary region and the measurement region, filling of the fluid channel and wetting of the test field may be optimized individually. Thus, generally, in a cross-section parallel to the direction of extension of the test elements and perpendicular to a layer setup of the test elements, as well as in a cross-sectional plane perpendicular to the axis of extension of the test elements, the fluid channel may have a geometry, such as a three-dimensional geometry, which may be adapted to the actual needs of transport and/or detection. Generally, the fluid channel may have a flexible and/or variable three-dimensional structure, in the capillary region and/or the measurement region.

Further advantages refer to the simplification of the manufacturing process.

Test Elements

Test elements are provided that incorporate the inventive concept, where such test elements include a housing that includes at least one base element and at least one cover element. As used herein, "housing" means an arbitrary mechanical structure providing a support for the features of the test elements described herein. Typically, the housing includes a layer setup, with the base element and the cover element being layers of the layer setup. In some instances, the housing is a strip-shaped housing and can even be a flexible, strip-shaped housing or a deformable, strip-shaped housing. As will be outlined in further detail below, the housing may fully or partially be made of a plastic material. In other instances, all components of the housing are flexible and/or deformable components, such as film components. Thus, and as described in more detail below, the base element and the cover element both can be fully or partially flexible, such as made of one or more foils. Other embodiments are feasible.

As used herein, "base element" means an arbitrary element providing a basis for a setup of further elements of the test elements described herein. Thus, the base element may form the lowermost element of the test elements. The base may be a strip-shaped element, such as a base strip. In some instances, the base is fully or partially made of a plastic material. However, the base may include a multiplicity of materials, such as a layer setup of one, two or more layers.

The base element may fully or partially be made of a plastic material. Examples of plastic base element materials include, but are not limited to, a polyethylene terephthalate foil; polycarbonate foil; polystyrene foil; polyvinyl chloride foil; polypropylene foil; poly(methyl methacrylate); a polyurethane foil; a polyester foil. Other materials or combinations of the named materials and/or other materials are feasible.

The base element may be formed by a carrier foil. In some instances, the carrier foil can have a thickness of about 50 µm to about 800 µm, of about 100 µm to about 500 µm, or even of about 250 µm. In some instances, the base element may have a shape that defines a basic footprint of the test elements. For example, the base element may have a rectangular shape such as a strip. Moreover, the base element may include a single-layer setup or may include a multi-layer setup having a multiplicity of layers, such as a laminate.

As used herein, "cover element" means an element that fully or partially covers the test element to fully or partially cover a fluid channel and/or other fluidic structures of the test elements described herein. Additionally or alternatively, the cover element may provide mechanical protection and/or protection against environmental influences onto the test elements, such as a moisture protection and/or a protection against mechanical damaging.

In addition, the test elements include at least one fluid channel formed within the housing, where the fluid channel includes a capillary region and a measurement region. As used herein, "fluid channel" means a fluidic structure adapted for transporting and/or guiding fluids, such as body fluids. The fluid channel may have one or more channel sections and/or one or more channels and/or tubes.

As used herein, "formed within the housing" means the housing and/or parts thereof form at least one wall of the fluid channel. The fluid channel typically is a closed fluid channel, which in any direction perpendicular to a flow of the fluid, is closed by walls of the fluid channel, such as by components of the housing.

As used herein, "capillary region" means a part of the fluid channel that fully or partially functions as a capillary element. Thus, the fluid channel may include one or more capillary regions, each capillary region having one or more capillary elements. As discussed above, the capillary element typically is a closed capillary element, which in any direction perpendicular to a direction of flow, is closed by walls of the capillary element. Additionally or alternatively, however, the at least one capillary region may as well fully or partially be formed as an opened capillary.

In some instances, the capillary region includes one straight capillary element, where the capillary region is adapted to transport the body fluid by capillary action, such as from an application position (e.g., an application opening) to a measurement region. As such, the capillary region may lead from an application opening directly or indirectly to the measurement region, non-withstanding the fact that, between the capillary region and the measurement region, at least one transition region may be positioned, as discussed above. In some instances, the capillary region may be a closed capillary, including an open channel in the base element, which fully or partially is covered by the cover element, thereby forming the closed capillary.

As used herein, "measurement region" means an arbitrary space of the fluid channel that is adapted to perform a measurement and/or in which a measurement may be performed. Thus, the measurement region may be adapted such that, by using the body fluid collected within the measurement region, the at least one analyte may be detected, as will be outlined in further detail below.

In some instances, the measurement region includes one or more chambers adapted for collecting the body fluid. Thus, the measurement region may have one or more widened chambers, with a widened cross-section when compared to the capillary region, in which the body fluid may be collected for the purpose of measurement. The at least one collection chamber may form an end portion of the fluid channel, such that the capillary region may transport body fluid from an application position, such as at least one application opening, to the chamber of the measurement region. Still, the measurement region, such as the collection chamber of the measurement region, may have or may provide one or more venting openings and/or venting channels, to support capillary transport via the capillary region from the application position into the measurement region. Thus, for example, the measurement region may include a collection chamber, where at one end of the collection chamber, the capillary region, such as one or more capillary elements of the capillary region, are connected to the collection chamber, and where at an opposing end, one or more venting openings and/or venting channels are provided to vent excess air from the collection chamber when the measurement region fills with the body fluid.

In some instances, the measurement region includes a widened reservoir (or collection chamber) of the fluid channel. Thus, as discussed above, the widened reservoir may include a widening of the fluid channel, for collecting larger amounts of body fluid. In other instances, the measurement region may have an essentially rectangular shape. However, other shapes are generally feasible.

The capillary region and the measurement region have differing aspect ratios. Thus, the capillary region may have at least one portion having a first aspect ratio, and the measurement region may have at least one portion having a second aspect ratio, where the first aspect ratio is different from the second aspect ratio. As used herein, "aspect ratio" means a maximum depth of the respective element, divided by the maximum width of the respective element. Thus, the aspect ratio of the capillary region, at a specific point of the capillary region, is defined by a quotient of the maximum depth of the capillary region, divided by a maximum width of the capillary region. For example, a lateral extension of the test element, such as a longer side of the test strip, may define a z-coordinate, wherein, at a specific z-coordinate, a cross-section of the capillary region is taken. The test elements may define a plane of extension, such as when the test elements are a test strip or a test tape. An x-dimension may be defined as a direction perpendicular to the plane of extension, such as perpendicular to a layer setup of the test strip. A y-coordinate may be a coordinate perpendicular to the z- and x-coordinates. Thus, a cross-section of the capillary region may be taken in the x-y-plane. The depth of the capillary region, in this case, is a maximum extension of the cross-section in the x-direction. Similarly, the width of the capillary region is the maximum extension of the cross-section in the y-direction. The ratio of the capillary region then may be defined as the ratio of the maximum depth, divided by the maximum width of the capillary region.

Similarly, with the same coordinate system, the aspect ratio of the measurement region may be defined as a maximum depth of the measurement region, divided by the maximum width of the measurement region, such as in a cross-sectional plane perpendicular to the z-axis.

With respect to the aspect ratios of the capillary region and/or the measurement region, in some instances, the capillary region may have an aspect ratio of about 0.1 to about 1.5, of about 0.2 to about 1.0 and, or even of about 0.3 to about 0.4, where the aspect ratio of the capillary region is defined by a maximum depth of the capillary region, such as at a specific z-coordinate, divided by a maximum width of the capillary region, such as at the specific z-coordinate. In this case, the z-coordinate may be defined as a coordinate along a direction of flow of the body fluid through the capillary region and/or as a direction parallel to an extension of the test element.

As used herein, "about" means within a statistically meaningful range of a value or values such as, for example, a stated aspect ratio, concentration, length, width, height, angle, weight, molecular weight, pH, ratio, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

Similarly, the measurement region may have an aspect ratio of about 0.005 to about 0.2, of about 0.01 to about 0.1, of about 0.02 to about 0.06, or even of about 0.04. The aspect ratio of the measurement region may be defined by a maximum depth of the capillary region, such as at a specific z-coordinate, divided by a maximum width of the measurement region, such as at the specific z-coordinate. For example, the z-coordinate may be a coordinate along a direction of filling of the measurement region and/or a direction of extension of the test element.

Taken together, the capillary region may have an aspect ratio of about 0.01 to about 1.5, and the measurement region may have an aspect ratio of about 0.005 to about 0.2. In some instances, however, the capillary region may have an aspect ratio of about 0.2 to about 1.0, and the measurement region may have an aspect ratio of about 0.01 to about 0.1. In other instances, the capillary region may have an aspect ratio of about 0.3 to about 0.4, and the measurement region may have an aspect ratio of about 0.02 to about 0.06.

Alternatively, the aspect ratio of the capillary region may exceed the aspect ratio of the measurement region by a factor of about 2 to about 20, by a factor of about 5 to about 15, or even by a factor of about 9 to about 10. Thus, the aspect ratio of the capillary region may be about 2 to about 20 times the aspect ratio of the measurement region, about 5 to about 15 times the aspect ratio of the measurement region, or even about 9 to about 10 times the aspect ratio of the measurement region.

In the capillary region, the fluid channel may have a maximum width, such as a maximum width of a cross-section taken at a specific z-coordinate (where, as in the cases cited above, the specific z-coordinate generally may be chosen arbitrarily), of about 100 µm to about 1.0 mm, a maximum width of about 200 µm to about 800 µm, or even a maximum width of about 300 µm to about 500 µm.

Similarly, in the measurement region, the fluid channel may have a width of about 500 µm to about 2.5 mm, a width of about 1.0 mm to about 2.0 mm, or even a width of about 1.6 mm to about 1.8 mm.

Taken together, the capillary channel may have a maximum width of about 100 µm to about 1.0 mm, and the measurement region may have a maximum width of about 500 µm to about 2.5 mm. In some instances, however, the capillary region may have a maximum width of about 200 µm to about 800 µm, and the measurement region may have a maximum width of about 1.0 mm to about 2.0 mm. In other instances, the capillary region may have a maximum width of about 300 µm to about 500 µm, and the measurement region may have a maximum width of about 1.6 mm to about 1.8 mm.

With respect to the shape of the fluid channel in the capillary region, in some instances, the fluid channel may have a cross-sectional shape such as in a plane perpendicular to the above-mentioned z-axis selected from a trapezoidal shape with the longer side of the trapezoid facing towards the cover element; a U-shape; or a V-shape. Additionally or alternatively, other shapes are possible. In addition, the capillary region may have a constant shape such as a constant shape from an application position to the transition region and/or to the measurement region. However, other varying shapes are feasible.

The direction of flow or a main direction of flow of the body fluid within the capillary region may be oriented parallel to the longitudinal axis of the test elements. Thus, for example, the capillary may comprise one or more capillary channels oriented parallel to the longitudinal axis of extension. However, deviations from a parallel orientation are generally feasible including, for example, deviations from a parallel orientation by no more than about 20°, by no more than about 10°, or even by no more than about 5°.

Returning to the cover element, it can include at least one test field having at least one test chemical, where the test chemical is adapted to change at least one optically measurable property in the presence of the analyte. As used herein, "test field" means a coherent amount of the test chemical. For an example, the test field may include a two-dimensional, laterally coherent amount of the test chemical. In some instances, the test field is oriented parallel to a plane of extension of the test element, such as to a plane of the test strip and/or test tape. Thus, with the coordinate system defined above, the test field may extend in the y-z-plane. Still, other setups are feasible.

The at least one test field may be a layer setup having one, two or more layers. Thus, the test chemical may form a test chemical layer of the test field. Additionally, other layers may be present, such as one or more separation layers that are adapted to separate cellular components of the body fluid, such as red blood cells. For example, the test field may be the layer setup with the test chemical forming a test chemical layer facing away from the body fluid and with an additional separation layer interposed in between the test chemical layer and the body fluid, such as interposed in between the test chemical layer and the measurement region. In this manner, the test field may include a carrier foil, where the test field is applied to the carrier foil. Therein, a first test chemical layer is applied to the carrier foil and, covering the test chemical layer, a separation layer may be deposited on top of the test chemical layer. However, other embodiments are feasible. For example, the separation layer may be one or more pigments, such as one or more white pigments, which, besides separating of the cellular components of the body fluid, may provide a white color background to simplify optical measurements through the carrier foil and to shield the intense red color of the red blood cells from the detector. Examples of suitable pigments include, but are not limited to, inorganic pigments, such as titanium dioxide.

As used herein, "test chemical" means an arbitrary chemical compound or mixture of compounds adapted to change at least one measurable property, in this case at least one optically measurable property, in the presence of the analyte. For further definitions of the test chemical and/or for further examples of the test chemical, reference may be made to the prior art section above. The test chemicals disclosed in these prior art documents generally may also be used within the present disclosure. As discussed above, the test chemical can be an optical test chemical adapted to change at least one optically measurable property, such as at least one color and/or at least one luminescence property, in the presence of the analyte. The optically measurable property and/or a change of the optically measurable property may be measurable by an arbitrary optical means, such as by means of one or more of the following optical measurements: a color measurement; a reflection measurement; a scattering measurement; a luminescence measurement, specifically a fluorescence and/or phosphorescence measurement, such as by exciting the test chemical with at least one excitation light and measuring luminescence light.

In some instances, the test chemical may include at least one enzyme and/or at least one coenzyme adapted to react with the at least one analyte to be detected. For example, reference may be made to the test chemicals disclosed in Intl Patent Application Publication No. WO 2007/118647. Further, with regard to test chemicals that may be used within the present disclosure, reference may be made to the test chemicals disclosed in Intl Patent Application Publication Nos. WO 2007/012494, WO 2010/094426, WO 2010/094427, as well as von Ketteler et al. (2012) ChemPhysChem. 13:1302-1306. These test chemicals, also referred to as cNADs, are highly stable against moisture and increased temperatures. These test chemicals may be used in an isolated fashion and/or in combination with other test chemicals.

Thus, for example, at least one enzyme and/or coenzyme may be present and adapted to perform a detection reaction with the analyte and/or in the presence of the analyte, whereby redox reactions, a color and/or a luminescence property of at least one dye that may be in the test chemical may change. For example, the at least one enzyme may be glucose oxidase and/or glucose dehydrogenase.

The test chemical can be adapted for appropriate optical detection reactions to detect the at least one analyte. For this purpose, the test field shall be accessible to body fluid. For example, the test field may be accessible to body fluid collected in the measurement region. In some instances, the test field may form at least one wall of the measurement region. That is, three or more of the walls of the measurement region may be formed by the base element, the base element thereby forming a trough for collecting the body fluid. A cover wall or roof of the measurement region, however, may fully or partially be formed by the at least one test field.

The cover element can be mounted to the base element by using at least one adhesive, where the adhesive contacts the test field. As used herein, "adhesive" means a material or a mixture of materials adapted to connect two or more elements by one or more of a material connection, a bonding, a material engagement and adhesion. For example, an adhesive may include one or more organic materials adapted to provide adhesive forces between two elements to be connected by the adhesive. In some instances, the adhesive material may include one or more polymeric materials, such as one or more polymer layers. An adhesive often is referred to as a glue.

As discussed above, the adhesive contacts the test field. In this manner, the adhesive is interposed in between the test field and the base element, where the adhesive fully or partially covers the test field. Thus, the adhesive is in direct contact with a test field surface or a part of the test field surface of the test field.

In some instances, the adhesive may be or may include a thermally activatable adhesive. The thermally activatable adhesive may have a non-adhesive state and may be activated by thermal activation, thereby bringing the activatable adhesive from the non-adhesive state into an adhesive state. Thus, for example, the adhesive may include one or more polymers and/or one or more polymer mixtures that may be activated by thermal activation. The activation may be reversible, such as by simple setting and/or additional actions such as cooling, thereby bringing the adhesive back into the non-adhesive state, again.

The thermally activatable adhesive may be activated by applying temperatures of about 60° C. to about 100° C., of about 70° C. to about 90° C. Heat application may be performed by using thermal plates, ovens, infrared heaters or other infrared sources or contact heaters. The application of heat is generally known in mass manufacturing, and standard means for heating may be used.

In some instances, the adhesive may have hydrophilic properties. Thus, for example, in a dry state or in a non-adhesive state, the adhesive may have a contact angle with water of below about 45° or even of below about 40°. In other instances, a contact angle of about 20° C. to about 40° C. may occur.

The adhesive may at least partially cover the walls of the fluid channel. For example, the adhesive may be large-area coated over the base element, thereby coating one or more surfaces of the base element facing towards the cover element, and, additionally, fully or partially coating one or more walls of the capillary region and/or one or more walls of the measurement region, preferably one or more walls formed within the base element. Thus, when a hydrophilic adhesive, such as a hydrophilic thermally activatable adhesive, is used, the adhesive itself may be used for generating one or more hydrophilic layers within the fluid channel. Besides the effect that a precise patterning of the adhesive is not necessarily required, the hydrophilic adhesive may serve the additional purpose of generating and/or enhancing hydrophilic properties of the fluid channel.

A plurality of adhesives is known, including hydrophilic adhesives. In some instances, one or more adhesives on a polyurethane basis may be used. In other instances, reference may be made to the urethane dispersion as disclosed in U.S. Pat. No. 5,759,364. This urethane dispersion, which may include one or more surfactants, may be used herein.

For potential mixtures of the dispersible polyurethane and/or polyurethane dispersion, reference may be made to the exemplary embodiments described herein. Further, as will be outlined in further detail below, commercially available adhesives, such as commercially available thermally activatable and/or hydrophilic adhesives, may be used, such as aqueous polyurethane dispersion "Dispercoll® U 56", available by Bayer MaterialScience LLC (Pittsburgh, USA). Additionally or alternatively, however, other types of adhesives may be used.

As noted above, the at least one cover element may include one or more components. In case a plurality of components is used for the cover element, this plurality of components may be positioned on top of each other or next to each other. In some instances, the at least one cover element includes at least two separate components. For example, the at least one cover element may include at least one cover foil that at least partially covers the capillary region. Further, the at least one cover element may include at least one test film, where the test film has the at least one test field, and where the test film fully or partially covers the measurement region. In some instances, the cover foil and the test film at least partially are positioned next to each other, such that both the cover foil and the test film are attached to the base element by using the at least one adhesive. Thus, both the test film and the cover foil may be glued to the base element by using the at least one adhesive. The test film and the cover foil may be separate elements, which, during manufacturing, may be provided individually and separate from each other.

Alternatively, the cover foil and the test film may be arranged in various ways. For example, the cover foil and the test film may be arranged in an adjoining fashion next to each other on top of the base element. Additionally or alternatively, the cover foil may fully or partially overlap the test film. Advantageously, a precise positioning of the cover foil and the test film, such as by using one or more additional positioning aids, is not necessary.

In some instances, the cover foil may be a plastic foil. Examples of suitable plastic foils include, but are not limited to, a polyethylene terephthalate foil; polycarbonate foil; polystyrene foil; polyvinyl chloride foil; polypropylene foil; poly(methyl methacrylate); a polyurethane foil; and a polyester foil. Other materials or combinations of the named materials and/or other materials are feasible. In other instances, the carrier foil may be a transparent plastic foil. Examples of suitable transparent plastic foils include, but are not limited to, a polyethylene terephthalate foil; polycarbonate foil; polystyrene foil; polyvinyl chloride foil; polypropylene foil; poly(methyl methacrylate); a polyurethane foil; and a polyester foil. Other materials or combinations of the named materials and/or other materials may be possible. Regardless, the cover foil may have a thickness of about 30 µm to about 150 µm or even of about 50 µm to about 100 µm.

Similarly, the test film may include a carrier foil, where the at least one test field is applied to the carrier foil and faces towards the measurement region. As outlined above, the test field may be a single-layer setup or a multi-layer setup. For example, at least one test chemical film is directly or indirectly applied to the carrier foil. The test chemical film may directly be exposed to the sample of the body fluid within the measurement region. Alternatively, the test chemical field or test chemical layer may be covered by one or more additional layers, such as one or more of the above-mentioned separation layers.

In some instances, the carrier foil may be a transparent foil, thereby allowing for performing optical measurements through the carrier foil. In other instances, the cover foil may be an intransparent or opaque cover foil. Similarly, the base element may fully or partially be an intransparent base element, such as an opaque base element.

The test field may include a large area coating of the carrier foil. The large area coating may extend laterally beyond the measurement region. For example, the test field may extend laterally beyond the measurement region, thereby providing one or more regions of the test field which, by using the at least one adhesive, are glued to the base element. Thus, the large area coating of the test field may extend from one lateral edge of the carrier foil to an opposing lateral edge of the carrier foil. This example allows for a simplified manufacturing technique, allowing for large area coating, without patterning of the test chemical, and allows for using a cutting technique for providing the test field.

In some instances, the cover element may fully or partially be coated by a hydrophilic coating, such as on a side facing towards the base element. In other instances, the cover foil and/or the carrier foil, each independently from each other, may fully or partially be coated by one or more hydrophilic coatings. For example, the above-mentioned hydrophilic adhesive may be used as a hydrophilic coating. Additionally or alternatively, however, other types of hydrophilic coatings are feasible, such as one or more coatings by using at least one surfactant.

Returning to the fluid channel, it can have at least two sections of differing depths. Thus, as outlined above, an axis of extension of the test element, which may be parallel to an axis of extension of the fluid channel, may define a z-axis. At a first coordinate of the z-axis, the fluid channel may have a first depth, and at a second z-coordinate being different from the first z-coordinate, the fluid channel may have a second depth, where the second depth is different from the first depth. Thus, along the z-axis, the depth of the fluid channel may vary, thereby creating a depth profile. The depth may even vary within the capillary region. The capillary region therefore may have at least two different z-positions, each having different depths. Additionally or alternatively, the capillary region may have a first depth, which may be constant and/or which may vary, where the measurement region may have a second depth that may be a constant second depth or a varying second depth, and where the first depth may be different from the second depth. In other words, the capillary region and the measurement region may have differing depths.

In some instances, the first depth (i.e., the depth of the capillary region) may be in a range of about 50 µm to about 300 µm, of about 100 µm to about 200 µm, and of about 140 µm to about 150 µm. Other dimensions are feasible. Likewise, the second depth may be in the range of about 15 µm to about 200 µm, of about 30 µm to about 100 µm, or even about 70 µm.

Alternatively, the first depth may be larger than the second depth. Thus, the capillary region has a larger depth than the measurement region. However, other embodiments are feasible. In some instances, the first depth (i.e., the depth of the capillary channel) may exceed the second depth (i.e., the depth of the measurement region) by a factor of about 1.3 to about 3, by a factor of about 1.5 to about 2.5, or even by a factor of about 2.

The capillary region may have a uniform depth. However, other embodiments are feasible, such as embodiments in which the capillary region has a varying depth, such as an increasing depth and/or a decreasing depth, when propagating from an inlet opening towards the measurement region.

The measurement region likewise may have a uniform depth. However, other embodiments are feasible, such as embodiments in which the measurement region may have an increasing depth and/or a decreasing depth, when following a path of filling of the measurement region by a sample of the body fluid.

The capillary region may be adapted to guide the body fluid, such as a predefined/predetermined/preset sample of the body fluid, such as a droplet of the body fluid, into the measurement region. The capillary region may directly feed the body fluid into the measurement region. Additionally or alternatively, however, the fluid channel may include one or more transition regions in between the capillary region and the measurement region. The transition region may be a region of the fluid channel adapted to provide an adaptation of a depth and/or a width and/or an aspect ratio of the capillary region to the measurement region. For example, in the transition region, a depth of the fluid channel may steadily change. In this manner, the depth steadily may decrease from the capillary region to the measurement region. For example, the capillary region may have a first constant depth, and the measurement region may have a second constant depth, with the first constant depth exceeding the second constant depth, such as by one or more of the above-mentioned factors. In the transition region, the depth may steadily decrease, in a direction of flow of the body fluid, from the capillary region to the measurement region.

In some instances, the depth of the fluid channel, in the transition region, may form a ramp, the ramp being a straight ramp or a curved ramp.

In view of the above, the test elements may have an elongated shape. For example, as an example, the test elements may have a strip shape. Accordingly, the test elements may have a longitudinal axis of extension, such as an axis of extension extending parallel to one of the sides of the test strips. More specifically, the test elements may have a rectangular shape, with a short edge and a long edge of the rectangular shape. For example, the longitudinal axis may be oriented parallel to one of the edges of the rectangle, especially parallel to the long edge of the rectangle.

Methods of Manufacturing Test Elements

Methods of manufacturing test elements are provided that incorporate the inventive concept. The methods can include the steps described herein, and these steps may be, but not necessarily, carried out in the sequence as described. Other sequences, however, also are conceivable. Furthermore, individual or multiple steps may be carried out either in parallel and/or overlapping in time and/or individually or in multiply repeated steps. Moreover, the methods may include additional, unspecified steps. Furthermore, one or more or even all of the steps may comprise substeps, where each of the substeps may be performed once or repeatedly.

Typically, however, the methods include at least the following steps:

a) providing the base element; and
b) mounting the cover element to the base element by using at least one adhesive, wherein the adhesive contacts the test field of the cover element.

As used herein, "provide" or "providing" means feeding a base element into the methods. At the time the base element is provided, the base element may be a ready-made base element, including all features of the base element. However, the providing of the base element may further include one or more steps of manufacturing and/or of refining of the test element. For example, as will be discussed in further detail below, the step of providing the base element may imply at least one method step of generating the fluid channel of the base element.

In some instances, method step a) may include the following substeps:

a1) providing a carrier foil for the base element; and
a2) providing the fluid channel within the carrier foil by using at least one forming process.

Thus, as discussed above, method step a) may include one or more steps of manufacturing the fluid channel or, which shall be implied, at least one part of the fluid channel. In any event, at least a part of the fluid channel may be provided within the carrier foil, such as an open channel structure which, in method step b), will be covered by the cover element to complete the fluid channel.

As used herein, "forming process" means a method step of reshaping a given element. For example, the forming process may imply a mechanical forming such as one or more of a stamping, a punching, or an embossing. Additionally or alternatively, heat may be applied, such as by using one or more of a thermoforming process or a thermal stamping, also referred to as heat stamping. In some instances, the forming process is a non-cutting forming process. Additionally or alternatively, however, one or more cutting steps may be implied.

In particular, a thermal stamping may be used in the forming process, by using a heated stamp, to provide the at least one fluid channel. Therein, the capillary region and the measurement region may be provided in one forming step. Additionally or alternatively, however, parts of the fluid channel may be manufactured independently, such as in one or more additional forming steps. For example, a single stamping step may be used or a combination of stamping steps may be used.

The forming process may imply a mechanical shaping of the carrier foil. As used herein, "mechanical shaping" means a shaping by using at least one mechanical tool, such as a stamp and/or a dye. Besides forming the fluid channel, the mechanical shaping may provide additional functions and may be used simultaneously for shaping one or more additional elements of the test elements. For example, at least one cut and/or opening may be formed within the carrier foil such as at least one positioning hole. Thus, the test elements, such as test strips, may provide one or more positioning holes for positioning the test elements within a measurement device. The fluid channel or the part of the fluid channel and the at least one additional element may both be formed within method step a).

With regard to method step b) and the mounting of the cover element to the base element by using the at least one adhesive, this step may include the following substeps:

b1) applying the adhesive to the base element or the cover element or both; and
b1) pressing the cover element to the base element.

The application of the adhesive to one or both of the base element and the cover element may take place in a state in which the adhesive is in a deformable state, such as in a liquid state and/or a state of a paste.

The pressing of the cover element to the base element may both imply the possibility that the cover element is pressed onto the base element and the possibility that the base element is pressed onto the cover element or both. Thus, generally, the cover element and the base element may be pressed together, such as by using a lamination process. In this manner, substep b2) may include a lamination process.

The adhesive may be an activatable adhesive, such as a thermally activatable adhesive. As such, the thermally activatable adhesive may have a non-adhesive state, where the thermally activatable adhesive may be activatable by thermal activation, thereby bringing the thermally activatable adhesive in an adhesive state. The adhesive, after performing substep b1), may be in the non-adhesive state.

Before or during substep b2), the adhesive may be thermally activated. The activation may take place in at least one independent activation step, such as in an independent heating step by using one or more heating elements, such as one or more heating elements selected from contact heaters and/or infrared heaters.

Additionally or alternatively, the activation may take place during one or more other method steps or substeps. For example, the activation may fully or partially take place during a thermoforming process and/or during pressing the cover element to the base element. In this manner, a lamination process may be used, which implies both the application of pressure and the application of heat to one or both of the cover element and the base element. Thus, a lamination by using one or more lamination cylinders may take place, for applying both pressure and heat to one or both of the base element and the cover element.

The adhesive may be applied to the cover element or the base element or both by using one or more appropriate application techniques, such as one or more coating techniques. Thus, the adhesive may be applied by using one or more coating techniques selected from doctor blading, roller coating, printing, spraying, slot coating, dip coating, roll-to-roll, and slot-die coating. Therein, various printing techniques may be used, such as screen printing, flexo printing, offset printing or other printing techniques or combinations thereof.

The cover element may include one or more additional elements. Thus, and as discussed above, the cover element may include at least a cover foil and a test film, where the cover foil may fully or partially cover the capillary region and where the test film may fully or partially cover the test field. In some instances, a transition between the cover foil and the test film may be positioned in a transition region of the fluid channel. Consequently, when the cover element includes the at least one cover foil and the at least one test film, method step b) may include one or more substeps.

In this manner, method step b) generally includes mounting both the cover foil and the test film to the base element by using the adhesive. As such, the base element may fully or partially be covered by the adhesive. Further, additionally or alternatively, the cover element (i.e., the cover foil and the test film), each, independently from each other, may fully or partially be covered by the adhesive, before mounting the cover foil and the test film to the base element.

The mounting of the cover foil and the test film to the base element may take place in one and the same step. For example, both the cover foil and the test film may be provided as continuous elements to a lamination process, where in the lamination process, both the cover foil and the test film are mounted to the base element. Alternatively, separate mounting steps for the cover element and the test film may be used.

The step of mounting the cover foil and the test film to the base element may imply one or more positioning steps, in which the cover foil or the test film or both are aligned with respect to the base element. In some instances, the alignment may take place without using additional alignment aids, such as additional alignment elements that remain in the test element as parts of the test element. This option may be achieved, specifically, by using the above-mentioned thermally activatable adhesive, which during alignment can be in the non-adhesive state. Thus, since the adhesive is in the non-adhesive state, the cover foil or the test film or both may slide on top of the base element to allow for positioning correction during alignment.

The cover foil and the test film may be arranged in various ways. For example, the cover foil and the test film may be arranged in an adjoining fashion next to each other on top of the base element. In this manner, the cover foil may fully or partially cover the capillary region, and the test film may fully or partially cover the measurement region. One or more abutting edges and/or one or more slots separating the cover foil from the test film may occur. The one or more abutting edges and/or slots may be positioned in or above a transition region between the capillary region and the measurement region. For example, the base element may be a strip-shaped base element with a surface facing towards the cover element. The surface of the base element may be subdivided into a first area including the capillary region, the first area being covered by the cover foil, and a second area including the measurement region, the second area being covered by the test film. Thus, the cover foil and the test film, in combination, may fully cover the surface of the base element. However, additionally, one or more uncovered areas and/or one or more areas covered by additional parts of the cover element may be present.

In addition to the option of positioning the cover foil and the test film in an adjoining fashion next to each other on top of the base element, the cover foil and the test film at least partially may overlap. Thus, the cover foil may fully or partially overlap the test film. For example, an edge of the cover foil may overlap the test film. This overlapping fashion allows for reducing the alignment effort for the cover foil or the test film or both.

The methods described herein are fully suited for being implemented as a mass-manufacturing process. In this manner, the methods may include at least one reel-to-reel process. Thus, one or more of the method steps disclosed above may be realized by using continuous processes. For example, a plurality of cover elements and a plurality of base elements each may be provided by independent continuous webs. In particular, a first web may be used for providing the base elements, and at last one second web may be used for providing the at least one cover element. In case the cover element includes the above-mentioned cover foil and the above-mentioned test film, the cover foil and the test film may be provided by using separate webs. Other embodiments are feasible.

In some instances, a direction of transport and/or a direction of extension of the continuous webs may be perpendicular to a direction of lateral extension of the test elements. For example, the test elements or the respective portions of the continuous webs, which contribute to single test elements, may be oriented parallel to each other perpendicular to a direction of lateral extension of the respective webs.

After performing the above-mentioned method steps a) and b), the reel-to-reel process may imply at least one separation process. Thus, the separation process used for individualizing the single test elements may imply one or more cutting processes, such as one or more dye cutting processes and/or one or more laser cutting processes. Other cutting techniques may be used.

In case a continuous test film is provided by using a continuous test film web, the test film web can be fully covered by the test field and/or include a continuous stripe of the test film. In this manner, no patterning of the test film may have to be applied in a direction of a transport of the continuous web. In this case, the test film extends from one lateral edge of the test element to the opposing edge. Thus, the lateral edges of the test field simply may be defined by the above-mentioned individualization process, such as the cutting process, without the need of additional patterning of the test field, thereby simplifying the process.

The accessible area of the test field, which is accessible to the sample fluid, may be defined by the region in which the test field covers the measurement region. In this accessible area, the above-mentioned optical detection reaction may take place.

For manufacturing three-dimensional structures in the fluid channel, standard manufacturing techniques may be used, such as embossing and/or stamping. These techniques may be used for manufacturing single test elements, for batch manufacturing, or for continuous manufacturing. Three-dimensional profiles of the fluid channel, specifically of the capillary region of the fluid channel, specifically with varying dimensions over the entire length of the capillary region, may be used for optimizing the filling time of the test elements (i.e., for optimizing the time span between application of a sample of the body fluid and a sufficient filling of the measurement region for performing an optical test).

With regard to an optimized filling time, a number of conditions may be fulfilled, such as an at least essentially square or round cross-section of the capillary region for optimized behavior in the capillary region and a flat rectangular cross-section beneath the test field. Thus, as outlined above, the geometries may be optimized individually. For example, a depth of about 70 µm beneath the test chemistry may be realized, as opposed to increased capillary channel openings for sufficient sample application. Further, the sample volume sufficient for performing a single analysis may be kept at a low level, such as at a level of below about 1 µl or even at a level of approximately about 800 nl.

For optimum capillary transport, a cross-sectional area of the capillary region may be kept constant from an application position to the measurement region and/or a transition region. With a capillary width of ≥0.2 mm, filling times may be shortened by a factor of 2. Further, a length of the capillary region, such as a length of a capillary channel from an application position to the transition region and/or to the measurement region, may be kept at approximately about 8 mm (e.g., about 8 mm±2 mm, or even about 8 mm±1 mm).

As outlined above, the use of a forming technique, such as the use of one or more of a stamping or embossing technique, specifically embossing and/or stamping one or more capillary regions or parts thereof into the base element, is highly advantageous over alternative techniques such as molding techniques like injection molding, or etching techniques. Thus, the method is performed without using any molding and/or etching. Avoiding molding and/or etching allows for large-scale manufacturing, such as in a reel-to-reel process. Further, and as also discussed above, the forming technique, such as one or more of stamping or embossing, leads to a high flexibility with regard to the structures of the fluid channel, such as the possibility of manufacturing three-dimensional structures of a capillary region.

Moreover, the use of the adhesive directly contacting the test field implies additional advantages, specifically when using a thermally activatable adhesive such as a thermally activatable polyurethane dispersion adhesive. For example, a positioning of the components of the test element may be simplified, and the use of additional alignment aids, such as additional positioning foils, may be avoided. Furthermore, the housing of the test element simply may consist of the base element and the cover element (i.e., may include a two-layer-setup that forms the fluid channel). Thus, the fluid channel may be composed of a two-layer-setup, with the base element as a lower housing element and the cover element covering the base element and with only the adhesive interposed in between. In this manner, no spacer element is required, such as a spacer foil, interposed in between the base element and the cover element, as in the present capillary structures. Thus, a bottom and walls of the fluid channel may be formed fully and in one piece by the base element, whereas the cover element, especially a flat cover element, simply covers the fluid channel. The walls of the fluid channel therefore may simply be formed by two elements (i.e., the base element in conjunction with the cover element). Additional elements for forming the walls of the fluid channel are not required and may be omitted.

It should be noted that when using a thermally activatable adhesive, a precise alignment of the components of the test elements is possible, without providing an additional alignment element, such as an alignment foil, for covering a slot in between a cover foil and a test film of the cover element. Both an adjacent positioning of the cover foil and the test film as well as an overlapping positioning of these elements is possible. Since the thermally activatable adhesive may be in a non-adhesive state during alignment, the elements may be aligned without any adhesive forces to be overcome.

In some instances, the adhesive is in direct contact with the test field, thereby fully or partially covering the test field. The adhesive itself may provide hydrophilic properties, enhancing wetting of the test field and/or enhancing capillary actions of the fluid channel and/or parts thereof. The use of additional hydrophilic coatings and/or surfactants, requiring one or more additional application steps, may be omitted, which further simplifies the manufacturing process.

Generally, the setup of the test elements and the manufacturing process as disclosed herein may be simplified to a large extent, as compared to conventional test elements and manufacturing processes. For example, a spacer element for forming walls of the capillary region may be omitted. Moreover, due to the generally variable and possibly three-dimensional structure of the fluid channel, the amount of sample of the body fluid required for one measurement may be reduced, since, by using the above-mentioned manufacturing process, smaller capillaries may be established. Furthermore, the number of parts for manufacturing the test elements and the complexity of the components of the test element may be reduced. Thus, since a spacer element may be avoided, the use of double-sided adhesive tapes, including appropriate liner elements for covering the adhesive sides, may be avoided.

Further, and as discussed above, an additional alignment element may be avoided, such as an alignment element in a gap between the cover foil and the test film. By using the above-mentioned techniques, specifically by forming the fluid channel fully or partially within the base element, without the necessity of forming side walls by using appropriate spacer elements, a low width of the capillary region may be achieved. Thus, a width of less than about 0.8 mm is feasible, which, typically, is not feasible by using conventional cutting processes and by using conventional spacers. Consequently, the sample volume may be minimized, and the filling time of the test elements may be reduced.

For manufacturing the capillary and/or for providing a channel structure within the base element, as a part of the fluid channel, such as in method step a2) discussed above, simple mechanical forming processes may be used, such as stamping and/or punching and/or embossing. For this purpose, one or more mechanical tools may be used, such as a stamping tool and/or an embossing tool and/or a punching tool. The tool may include two or more components, such as a stamping component and a counter-component, where the base element may be positioned in between the two components of the tool. For example, the tool may include one or more of a stamp, a dye, a dye plate, and a stencil. Further, an appropriate counterpart may be provided, such as a counter-dye, a dye plate, a matrix, a counter-stencil, a template or a shaping dye or floating dye. Thereby, a three-dimensional structure of the fluid channel and/or of a part thereof may be provided in the tool. The stamping may take place at room temperature or at an elevated temperature.

By using the above-mentioned techniques, the fluid channel and/or a part thereof may be optimized with regard to geometry. For example, the capillary region may have a cross-section that may resemble a square and/or round cross-section. This cross-section with aspect ratios close to 1 enhances short filling times.

In contrast, the measurement region may be designed as a collection region. In this measurement region, a large area may be provided, providing a large interface between the liquid sample of the body fluid and a surface of the test field. This large area provides appropriate advantages with regard to positioning tolerances of the test element and/or the test field and therefore allows for a simplified optical measurement setup. To reduce the consumption of sample volume within the measurement region, the depth within the measurement region may be reduced as compared to the depth in the capillary region, thereby reducing the volume of sample fluid within the measurement region and reducing the filling time of the measurement region.

To provide an appropriate and fluidically optimized transition between the capillary region and the measurement region, the transition region may provide an appropriate shape. For example, a ramp may be provided and/or a spline-type transition region. Thus, in the transition region, steps and/or sharp edges may be avoided.

Further, using the forming technique, especially the cold forming technique at room temperature, may allow for manufacturing very tight capillary regions, such as having a width of below about 0.8 mm, such as a maximum width w of about 0.2 mm≥w<about 0.8 mm. Contrarily, when using conventional cutting techniques, the width typically is limited to a lower limit of 0.8 mm.

As discussed above, the forming process can be a cold forming process and/or include a cold forming process, such as a forming process at room temperature of about 21° C. or of about 24° C. The cold forming process can be selected from a stamping, a punching, and an embossing at room temperature. By using cold forming processes, a high speed of manufacturing may be established when compared to hot forming processes, such as hot stamping (which, however, is usable additionally or alternatively). This is mainly due to the fact that no heating or cooling phase during the forming process is required. Further, a dimensionally stable handling may be established.

The possibility of manufacturing capillary regions having an aspect ratio close to 1 or closer to 1 when compared to conventional cutting techniques provides a large number of advantages. Thus, three-dimensional capillaries having an essentially square or circular cross-section in the filling region generally provide a lower flow resistance at the same cross-sectional area of the capillary cross-section when compared to flat capillaries, such as flat capillaries having a ratio width/depth of >>3. For example, in case the capillary depth is increased from about 70 µm to about 140 µm, and the width is reduced from about 800 µm to about 400 µm, the filling time theoretically is reduced by a factor of 0.5, at the same volume of the liquid sample.

Further advantages refer to use of the adhesive, such as the thermally activatable adhesive and, more preferably, the polyurethane adhesive such as Dispercoll® U 56. Thus, commercially available adhesives, such as commercially available dispersions of adhesive, may be used and may be applied to one or more of the base element and the cover element, such as to a strip or foil of the base element. For applying the adhesive, simple application techniques may be used, such as for applying a dispersion of the adhesive. For example, a polycarbonate foil and/or a polyester foil, such as a polyethylene terephthalate (PET) foil, may be used for the base element, followed by the above-mentioned forming process for formation of a channel structure of the fluid channel, and followed by at least one step of application of the dispersion.

The application of the adhesive to the base element may be followed by one or more drying steps, such as for drying the at least one film of the adhesive dispersion. After drying, a non-adhesive layer may be generated on the base element, which, as an example, may be manufactured or processed in a reel-to-reel process. Thus, whole handling of the foil of the base element may be performed without the necessity of using one or more liners or liner films for covering the adhesive.

A further advantage of the test elements and methods of manufacture thereof as disclosed herein resides in the fact that, in a simple and efficient way, hydrophilic properties of the fluid channel or parts thereof may be provided. Thus, by using a hydrophilic adhesive such as the above-mentioned commercially available thermally activatable adhesive, hydrophilic surface properties may be provided, such as hydrophilic properties with a contact angle of about 37°. Thus, additional surfactants and/or additional treatments for increasing hydrophilicity may be omitted. Still, these additional surfactants and/or treatments may be applied. Thus, one or more surfactants and/or coatings may be applied, such as to the base element and/or to the cover element, in order to increase hydrophilicity. In this manner, one or more surfactants and/or one or more inorganic materials and/or inorganic coatings, such as coatings with dispersions of nano-materials such as nanosilica gel, may be applied to one or more of the base element or the cover element and/or parts thereof. These surfactants and/or inorganic materials having hydrophilicity-increasing properties may be applied as an independent layer and/or may be added to the adhesive.

The coating of the base element with the adhesive may take place before, during or after forming the fluid channel, such as a channel structure within the base element, specifically in a foil of the base element. For example, the forming of the fluid channel may take place by using a coated base foil, fully or partially coated with the adhesive.

As discussed above, the forming process for at least partially forming the fluid channel within the carrier foil of the base element, especially by using a cold forming process at room temperature, may, simultaneously or in conjunction, be used for adding additional functional elements to the base element, such as one or more holes and/or one or more apertures. The forming of the fluid channel, as turned out during numerous experiments, is, at least substantially, not affected and/or negatively influenced by the presence of the adhesive on the carrier foil of the base element. Thus, specifically, adhesive properties and/or hydrophilic functions were not deteriorated by the forming process.

The cover element, especially the cover foil and/or the test film, may, independently from each other or commonly, be fully or partially coated with the adhesive too, specifically with a hydrophilic adhesive and, more specifically, with the thermally activatable hydrophilic adhesive, such as Dispercoll® U 56 and/or other adhesives. Additionally or alternatively, other types of hydrophilic foils may be used as a cover element and may be mounted to the base element by using one or more adhesives.

The actual mounting process, such as the adhesive bonding, of the cover element and the base element, such as the cover foil, the test film and the carrier foil may take place by heating to about 70° C. to about 90° C. by using a line-process with one or more upstream infrared radiation sources and/or other heat sources, such as in a lamination process. Thus, a line-process may be implemented, with one or more heat sources, followed by one or more lamination devices, such as one or more lamination cylinders and/or one or more other types of laminators.

A transition of the cover foil to the test film may take place before the liquid within the fluid channel actually reaches the measurement region. For example, a transition between the cover foil and the test film may take place before the end of the capillary region is reached by the liquid propagating through the fluid channel. Thus, the high capillary force of the deep capillary channel may be used for transporting the body fluid, such as the blood, into the measurement region and/or onto the test field. As discussed above, additional positioning elements are not required. By combining a plurality of functions within one element of the test elements, components of the test elements may be omitted, and the overall layer setup may be simplified, by still maintaining or even improving the overall functionality of the test elements, such as with regard to filling time and/or reliability of wetting.

Further, the simplified setup and the improved wetting by using one or more hydrophilic adhesives, specifically without the necessity of applying additional surfactants, may improve reliability of the test elements with regard to leakage. Thus, in many conventional test elements, the requirement of using surfactants as well as the above-mentioned technical challenges of positioning various cover elements with regard to the base element may lead to unwanted egression of body fluids, such as at the end of a capillary channel and before reaching the actual test field. By improving the wetting properties, by providing appropriate capillary geometries, and/or by improving the alignment process, these leakage problems may be reduced or even fully avoided, thereby avoiding or at least reducing contaminations of a test device or measuring device using the test elements.

EXAMPLES

The inventive concept will be more fully understood upon consideration of the following non-limiting examples, which are offered for purposes of illustration, not limitation.

As shown in FIG. 1, an exemplary test element 110 for detecting at least one analyte in a body fluid is depicted in a perspective view. The test element 110 includes a housing 112 which, in this exemplary embodiment, may be made up of three elements. Thus, the housing 112 may include a base element 114 and a cover element 116, wherein the cover element 117 includes a cover foil 118 and a test film 120.

The base element 114 includes a carrier foil 122 with a fluid channel 124 formed therein, especially by using a forming process such as embossing and/or stamping. The fluid channel 124 may include a capillary region 126, an optional transition region 128, and a measurement region 130. The capillary region 126 is fully or partially covered by the cover foil 118, and the measurement region 130 is fully or partially covered by the test film 120. The capillary region 126 may be adapted to guide a body fluid sample from an application position 132, such as an application opening, to the transition region 128 and/or the measurement region 130.

The cover element 116 is fully or partially mounted to the base element 114 by using one or more layers of adhesive 134, which may fully or partially cover the base element 114 and/or the cover element 116. For example, a thermally activatable adhesive may be used, as discussed in the above-mentioned manufacturing process, such as Dispercoll® U 56, available by Bayer Material Science LLC, Pittsburgh, USA.

The carrier foil 122 may be or may include a polycarbonate plastic material, such as a black polycarbonate foil. For example, the carrier foil 122 may have a thickness of 200 µm.

Alternatively, the cover foil 118 may be a plastic foil, such as a polycarbonate foil having a thickness of 140 µm, coated with the adhesive 134, such as with as Dispercoll® U 56.

The test film 120 may include a carrier foil 136 which, on a side facing the base element 114, may be coated with a test field 138, the test field 138 including at least one test chemical film having at least one test chemical 140 and, optionally, having one or more additional layers, such as one or more separation layers. The test field 138 is in contact with the adhesive 134. In some instances, the carrier foil 136 of the test film 120 is large-area coated with the test field 138. The carrier foil 136 can be fully or partially transparent.

As can be seen in FIG. 1, the cover foil 118 and the test film 120 may be positioned adjacent to each other on top of the base element 114, such that the test film 120 and the cover foil 118 fully or partially cover the surface of the base element 114. However, one or more venting openings 142 may remain uncovered to allow for an egression of excess gas when filling the fluid channel 124 with body fluid.

The cover foil 118 and the test film 120 meet at a hem or abutting edge 144, which may be positioned outside the measurement region 130, such as in the transition region 128 and/or in the capillary region 126. At the abutting edge 144, a slot may occur, which may be kept as small as possible.

Figure 2:
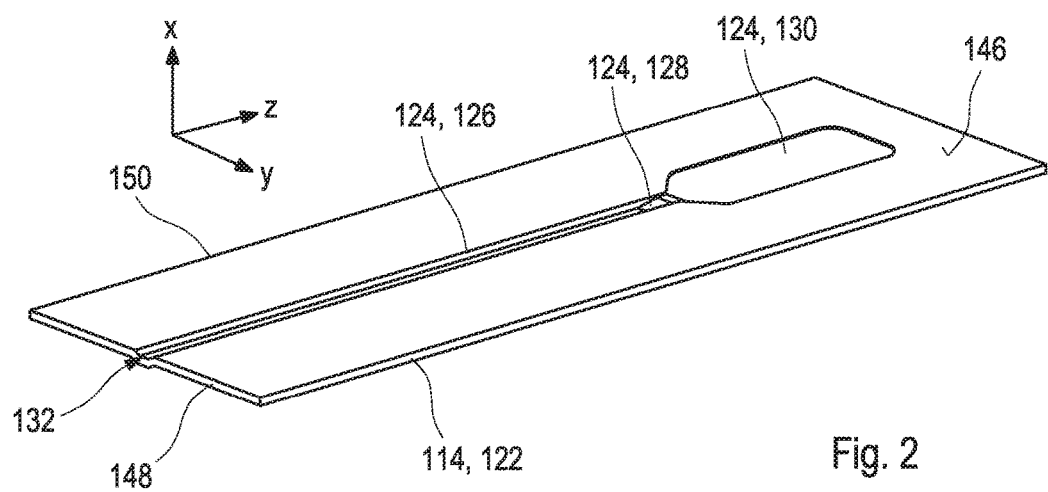
FIG. 2 shows a base element to be used in the test element of FIG. 1.

FIG. 2 shows a perspective top view onto the carrier foil 122 of the base element 114. In this perspective, a surface 146 of the carrier foil 122 is shown which, in the setup of FIG. 1, faces the cover element 116 and which, during manufacturing of the test element 110, is fully or partially covered by the adhesive 134. Further, the carrier foil 122 is shown in a semi-processed state, in which a structure of the fluid channel 124 is formed in the carrier foil 122. Thus, the setup of FIG. 2 shows a semi-processed product that may be manufactured from a flat carrier foil 122 by a forming process, such as an embossing and/or stamping process, especially at room temperature. As can be seen, the fluid channel 124 includes the capillary region 126 that extends towards the application position 132 located at an edge 148 of the carrier foil 122, to allow for an application of a body fluid sample. From the application position, via capillary forces, the body fluid sample is drawn into the measurement region 130, which forms a collection region for the body fluid.

As further can be seen in the setup of FIG. 2, the transition region 128 may form a ramp and/or another type of continuous and/or steady transition between the depth of the capillary region 126, which may be a constant first depth, to the depth of the measurement region 130, which, again, may be a constant second depth. As can be seen in FIG. 2, the second depth may be smaller than the first depth. However, other setups are possible, such as embodiments in which the depth within the capillary region 126 and/or the depth within the measurement region 130 are not constant. Further, instead of using a ramp for transition, other types of transitions may be used, such as a continuous and/or steady transition, or even a spline-shaped transition without steps, sharp edges or other unsteady or non-continuous points.

As discussed above, the capillary region 126 and the measurement region 130 have differing aspect ratios. This aspect will be explained with regard to FIGS. 3A to 3F below.

Figure 3:
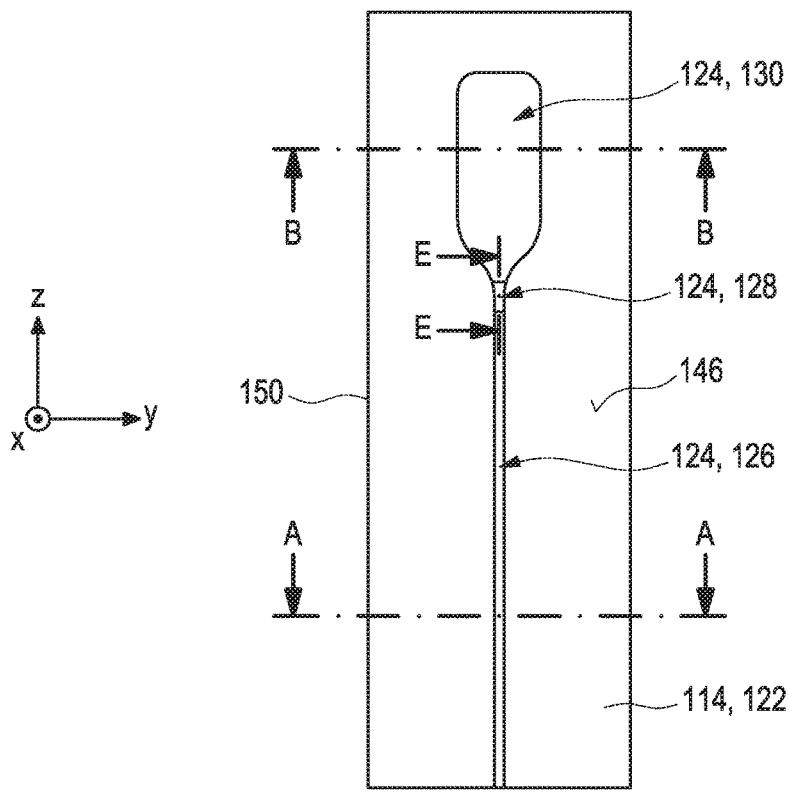
FIGS. 3A-3F show various views of the base element according to FIG. 2, where FIG. 3A show a top view onto the surface 146 of the carrier foil 122 is shown.
Figure 3:
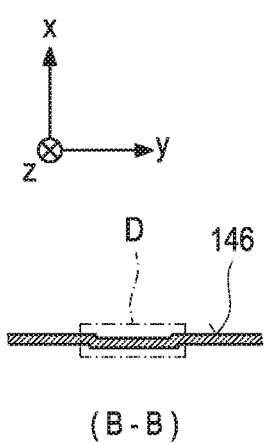
Figure 3:
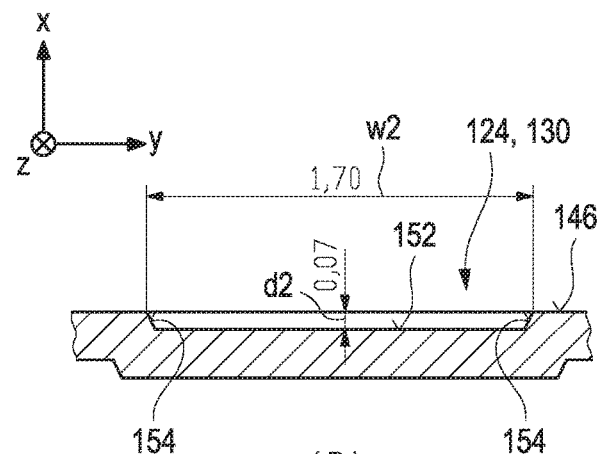
Figure 3:
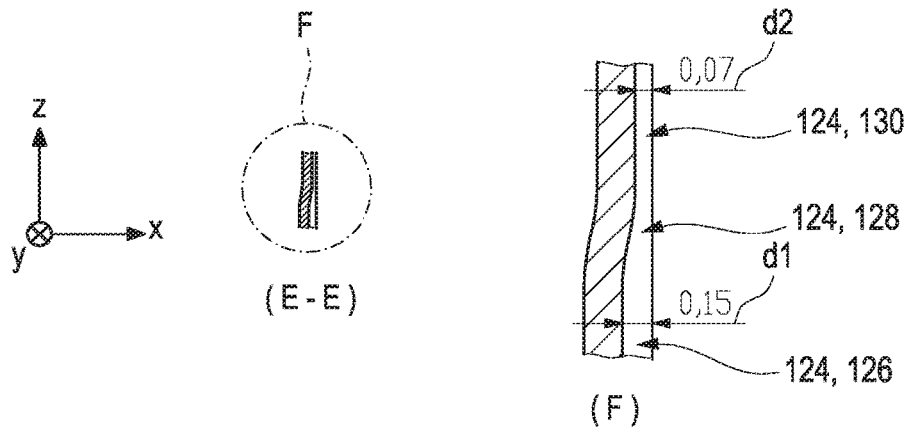
Figure 3:
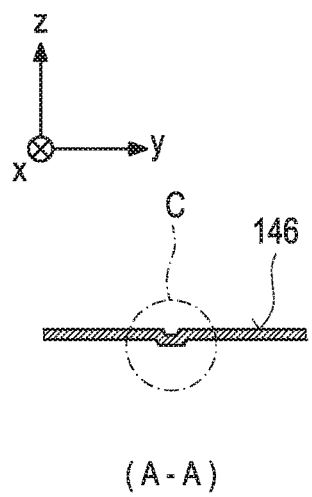
Figure 3:
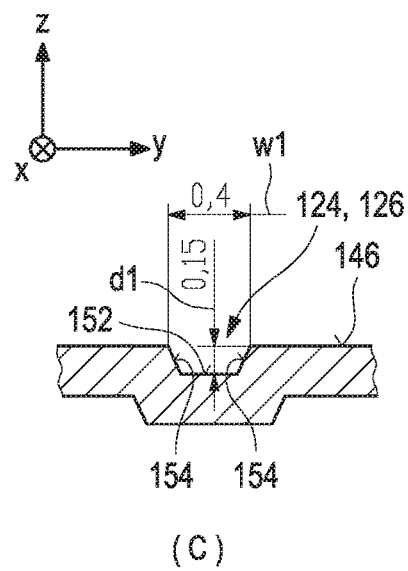

Thus, as shown in FIG. 2 or in FIG. 3A, one or more of an axis of extension of the capillary region 126, a direction of flow of the liquid within the capillary region 126 or a longitudinal edge 150 of the rectangular test element 110 and/or carrier foil 122 may define a longitudinal axis of the test element 110, also referred to as a z-axis. In FIG. 3A, a top view onto the surface 146 of the carrier foil 122 is shown. FIG. 3B shows a cross-sectional view of the carrier foil 122 along cutting line B-B in FIG. 3A, FIG. 3C shows an enlarged view of region D in FIG. 3B, FIG. 3D shows a longitudinal cross-section along the z-axis along cutting line E-E in FIG. 3A in two different magnifications (10:1 and 40:1), FIG. 3E shows a cross-sectional view along cutting line A-A in FIG. 3A, and FIG. 3F shows an enlarged view of region C in FIG. 3E.

With the z-axis as defined above and the plane of the carrier foil 122, a coordinate system may be defined. Thus, as can be seen in FIG. 3B, 3C, 3E or 3F, a direction perpendicular to the plane of the carrier foil 122 may be defined as the x-direction. A direction perpendicular to the z-axis and the x-axis, which is another dimension parallel to the plane of the carrier foil 122, may be defined as a y-dimension. Consequently, the cross-sectional views in FIGS. 3B, 3C, 3E and 3F are cross-sectional views in the x-y-plane, whereas the cross-sectional view in FIG. 3D is shown in the x-z-plane.

Further, in FIGS. 3C, 3D and 3F, exemplary dimensions of the fluid channel 124 are given in millimeters. It shall be noted, however, that other dimensions are feasible, such as dimensions deviating from the given dimensions by no more than 50%, no more than 30% or no more than 10%. Still, other geometries and/or dimensions are feasible.

In FIGS. 3E and 3F, cross-sectional views of the capillary region 126 are shown. Therein, a maximum width of the capillary region 126, which is the width close to the surface 146, is denoted by w1. A maximum depth of the capillary region 126 is denoted by d1. The maximum depth d1 is the distance between the surface 146 and the bottom 152 of the capillary region 126.

An aspect ratio of the capillary region 126, which also may be referred to as a first aspect ratio A1, may be defined as $A1 = d1/w1$. With the exemplary dimensions given in FIG. 3F, the aspect ratio may be 0.375. It shall be noted, however, that other aspect ratios are feasible.

Further, as can be seen in FIG. 3F, the cross-sectional shape of the capillary region 126 may have a trapezoidal shape. It shall be noted, however, that other cross-sections are feasible. In some instances, the cross-sectional shape is chosen such that the first aspect ratio a1 is as close as possible to 1. This aspect ratio may be achieved by a cross-sectional shape which is as close as possible to a square shape and/or a circular shape. By using the forming process, especially a mechanical forming process such as an embossing and/or a stamping process, a wide variety of cross-sectional shapes may be achieved.

In FIGS. 3B and 3C, as outlined above, a cross-section in the measurement region 130 is shown. Similar to the aspect ratio of the capillary region 126, a second aspect ratio may be defined, which is the aspect ratio of the measurement region 130, by dividing a maximum depth d2 by a maximum width w2 within the measurement region 130. Again, the maximum depth d2 is a distance between the surface 146 and the bottom 142 in the measurement region 130. With the exemplary dimensions given in FIG. 3C, the second aspect ratio $a2 = d2/w2$ is 0.041. As can be seen, the aspect ratio of the capillary region 126 is larger than the aspect ratio of the measurement region 130, in this case by a factor of approximately 9.1.

Further, as can be seen by comparing FIGS. 3C and 3F, d2 is lower than d1. Thus, specifically by using the mechanical forming process such as one or more stamping and/or embossing processes, a three-dimensional profile within the fluid channel 124 may be achieved to independently optimize the capillary region 126 for an optimum filling behavior and a small sample volume and to optimize the measurement region 130 for an optimum wetting of the test field 138 in the measurement region 130. To adapt the depth of the capillary region 126 to the depth in the measurement region 130, as can be seen in FIG. 3D, the transition region 128 may provide a continuous transition, especially by providing a ramp and/or another type of spline function, preferably without sharp edges.

As can be seen in FIG. 3C, the measurement region 130 may, similar to the capillary region 126, have a trapezoidal shape. Other shapes, such as shapes having round edges, are feasible, as for the capillary region 126.

As discussed above, surface 146, before and/or after the forming process for forming the fluid channel 124, may be coated with the adhesive 134. Thus, a dispersion of the adhesive 134 may be used. After application of the adhesive 134, which is not depicted in FIGS. 3A to 3F, the adhesive 134 may be subjected to one or more drying steps and/or one or more drying processes, such as in a continuous drying process. For this purpose, one or more heaters may be used, in order to evaporate one or more solvents from the dispersion. After the drying step, the adhesive 134 may be in a non-adhesive state and may be thermally activated before applying the cover element 116. Before thermal activation, the cover foil 118 and/or the test film 120 may be positioned correctly, as shown in FIG. 1. This positioning and/or alignment is simplified due to the fact that the adhesive 134 is in a non-adhesive state. Afterwards, a thermal activation may take place, before or in combination with applying pressure, in order to compress the layer setup as shown in FIG. 1.

The adhesive 134 may have hydrophilic properties. Thus, both in case the forming process of the fluid channel 124 takes place after applying the adhesive 134 and in case applying takes place after the forming of the fluid channel 124, the bottom 152 and/or walls 154 of the fluid channel 124 may fully or partially be covered with the hydrophilic adhesive 134. Additionally, the cover element 116, such as the cover foil 118 and/or the test film 120 may fully or partially be covered with the hydrophilic adhesive 134 and/or may have hydrophilic properties.

By appropriate three-dimensional shaping of the fluid channel 124 and optionally by applying hydrophilic properties, a filling behavior of the fluid channel 124 may be improved or even optimized. This will be shown with respect to FIGS. 4A to 4C below.

Figure 4:
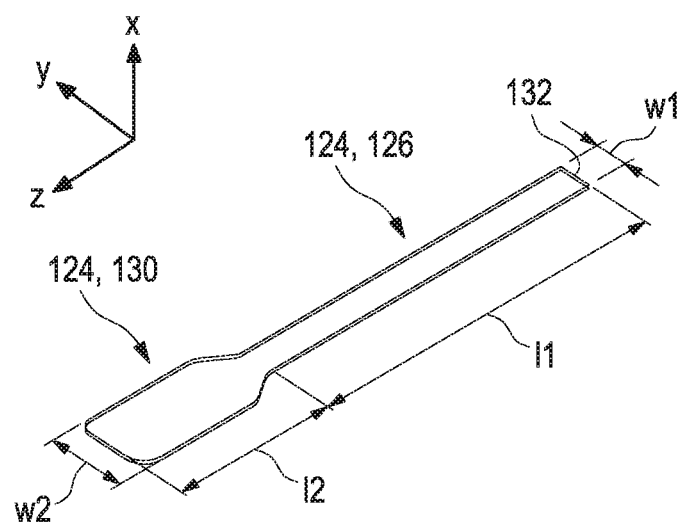
FIGS. 4A-4B show volumes of a fluid channel with a uniform depth (FIG. 4A) and a varying depth (FIG. 4B).
FIG. 4C shows filling curves for the fluid channels of FIGS. 4A and 4B.
Figure 4:
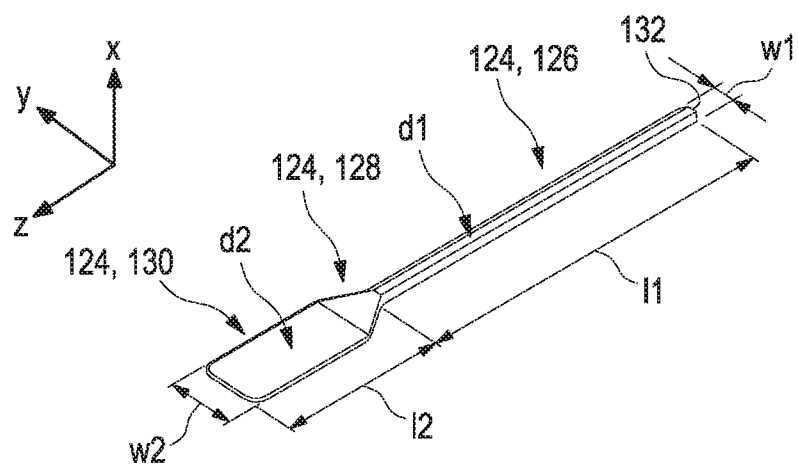
Figure 4:
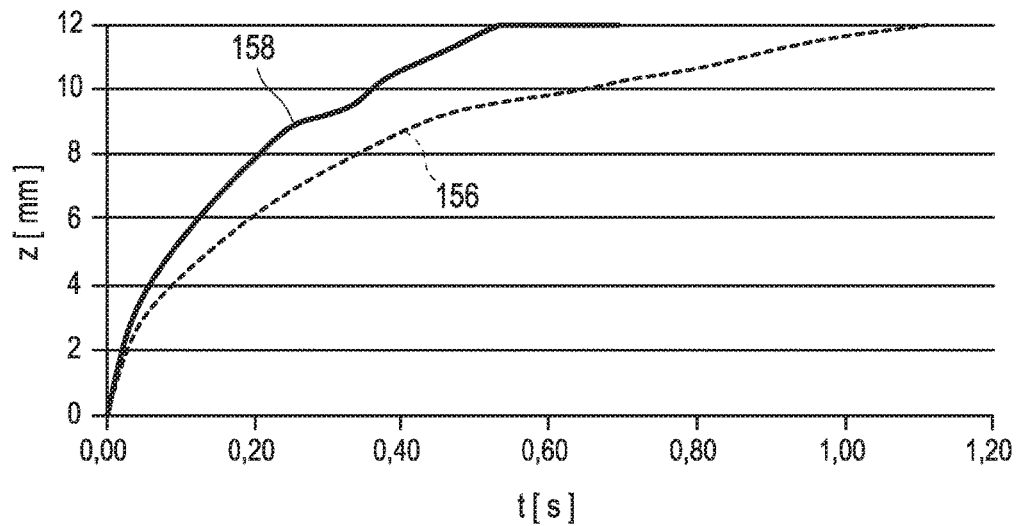

Specifically, FIG. 4A shows a fluid channel 124 having a uniform depth, both in the capillary region 126 and in the measurement region 130. In contrast, FIG. 4B shows a preferred setup having a three-dimensional structure of the fluid channel 124 with a non-uniform depth of the fluid channel 124. Thus, in the capillary region 126, as discussed with respect to FIGS. 3A to 3F above, a first depth d1 may be present, especially a uniform first depth, and in the measurement region 130 a second depth d2 may be present, especially a uniform second depth, which may be smaller than the first depth d1.

FIG. 4C shows measurement results for test elements having different geometries of the fluid channel 124. Therein, on the horizontal axis, the time after application of a sample of the body fluid to the application position 132 is denoted, given in seconds s. On the vertical axis, a progression along the z-axis, given in mm distance from the application position, is marked. Curve 156 denotes filling progression of a fluid channel 124 according to the embodiment shown in FIG. 4A, and curve 158 shows a filling behavior of a test element 110 having the preferred three-dimensional geometry of the fluid channel 124 of FIG. 4B.

The measurements were performed with test elements 110 as described herein with fluid channels 124 formed by an embossing process. In both cases, as the carrier foil 122, a black polycarbonate foil having a thickness of 200 μm was used. The carrier foil 122 was coated with Dispercoll® U 56. Subsequently, after drying of the adhesive film, the fluid channel 124 was formed by using a cold embossing process by using a hand-actuated pressing tool.

A test film 120 was applied, having a test field 138. A test chemical 140 including glucose oxidase as an enzyme was used. The test field 138 had an overall thickness of 80 μm.

As the cover foil 118, a polycarbonate foil having a thickness of 140 μm was used i. On a surface of the cover foil 118 facing the base element 114, the cover foil 118 was coated with the same adhesive 134 as the base element 114, followed by a drying step to provide a non-adhesive, smooth surface of the adhesive 134.

Further, the cover foil 118 and the test film 120 were positioned on top of the base element 114 in an abutting fashion. After this alignment step, a thermal activation by heating the layer setup to 75° C. was applied, and the cover element 116 thus was mounted to the base element 114 with the abutting edge 144 outside the measurement region 130.

Thus, the setups used for measurements 156 and 158 were identical except for the dimensions of the fluid channel 124. For the setup in FIG. 4A, corresponding to measurement curve 156, the following dimensions were used:

capillary region 126: d1=70 μm, w1=0.8 mm, l1=8.5 mm; and measurement region 130: d2=70 μm, w2=1.7 mm, l2=4 mm.

Therein, l1 denotes the length of the capillary region 126, and l2 denotes the length of the measurement region 130, both dimensions measured in z-direction.

In contrast, for the setup shown in FIG. 4B, having a non-uniform profile of the bottom 152 and different depths d1 and d2, the following dimensions were used:

capillary region: d1=150 μm, w1=0.4 mm, l1=8.5 mm; and measurement region: d2=70 μm, w2=1.7 mm, l2=4 mm.

In Tables 1 and 2 below, measurements for filling times of the capillary region 126 (first column), the transition region 128 (second column), the measurement region 130 (third column), and total filling times of the fluid channel 124 (fourth column) are given in seconds. The measurements were performed by using whole blood with heparin, the whole blood having a hematocrit of 43. For the setup of FIG. 4A, six measurements were performed; for the setup of FIG. 4B five measurements. In the last line of the Table, the mean value for the total filling time (last column) is given in each case.

TABLE 1

Filling times for test elements according to FIG. 4A.

| Time (s) Capillary region | Transition region | Measurement region | Total |
|---|---|---|---|
| 0.808 | 0.325 | 1.042 | 2.18 |
| 0.750 | 0.417 | 0.808 | 1.98 |
| 0.733 | 0.250 | 0.733 | 1.72 |
| 0.800 | 0.292 | 0.808 | 1.90 |
| 0.817 | 0.267 | 0.717 | 1.80 |
| 0.833 | 0.292 | 0.842 | 1.97 |
|  |  | MW | 1.92 |

TABLE 2

Filling times for test elements according to FIG. 4B.

| Time (s) Capillary region | Transition region | Measurement region | Total |
|---|---|---|---|
| 0.33 | 0.07 | 0.39 | 0.79 |
| 0.36 | 0.07 | 0.6 | 1.03 |
| 0.37 | 0.03 | 0.73 | 1.13 |
| 0.34 | 0.04 | 0.38 | 0.75 |
| 0.32 | 0.04 | 0.42 | 0.79 |
|  |  | MW | 0.90 |

As can be seen by comparing the curves in FIG. 4C and by comparing the mean values (MW) in Tables 1 and 2, the three-dimensional geometry of the fluid channel 124 of the test element 110 in FIG. 4B, having different depths d1 and d2, may lead to a significant shortening of the overall filling time. Thus, by using an appropriate geometry of the fluid channel 124, a significant improvement of the filling behavior and a significant shortening of the filling time or even an optimization of the filling behavior is possible. The three-dimensional geometry of the fluid channel 124, with adapted depth d1 and d2, is specifically feasible by using the above-mentioned forming process starting with a flat foil, such as a cold mechanical forming process, especially a cold stamping and/or embossing.

Figure 5:
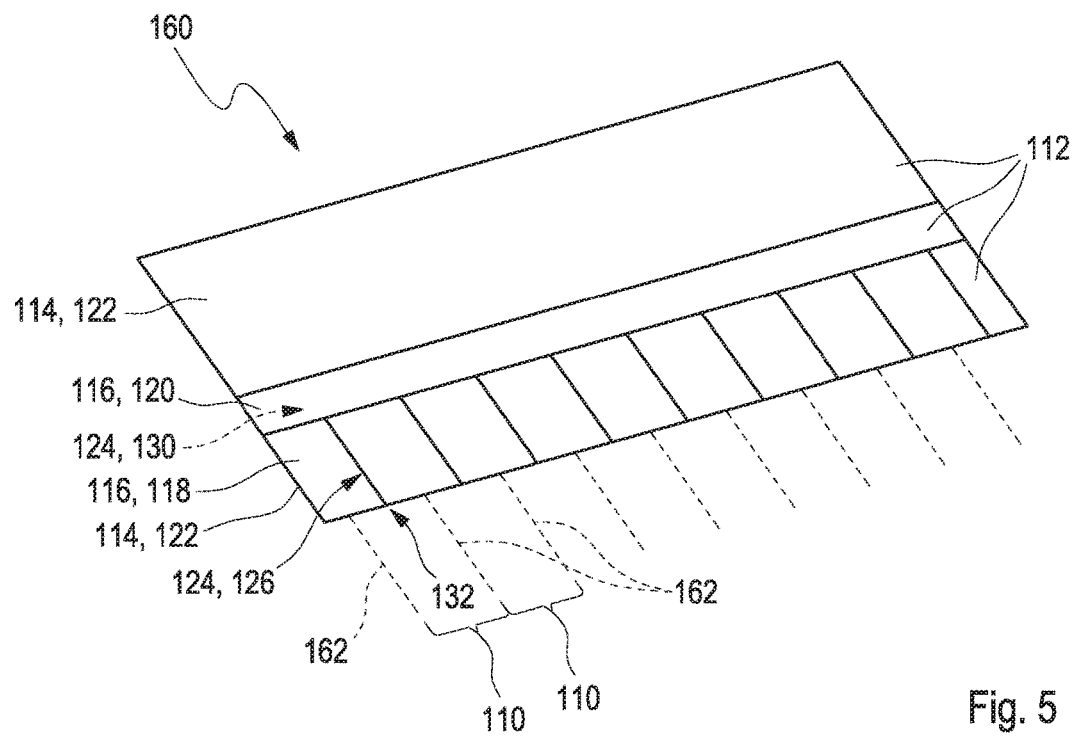
FIG. 5 shows a plurality of test strips manufactured by a reel-to-reel process.

To demonstrate that the methods described herein are well suited for mass manufacturing, especially by using reel-to-reel technology, several manufacturing experiments were performed. As shown in FIG. 5, a batch of test elements 110 manufactured by reel-to-reel processing is depicted before individualization of the test elements. The test elements 110 are manufactured as a test element web 160. Dotted lines in FIG. 5 denote virtual cutting lines 162 along which an individualization of the single test elements 110 by cutting may take place.

As also shown in FIG. 5, the carrier foil 122 may be provided as a continuous web, followed by a coating with the adhesive (not depicted) and a drying step. Further, the cover foil 118 and the test film 120 may be provided as continuous webs and also may be coated with the adhesive 134, and may be subjected to a drying step. The carrier foil 120 may be subjected to a mechanical forming step, especially a continuous mechanical forming step, such as a punching and/or embossing step, at room temperature. Subsequently, a thermal activation of the adhesive may take place, and the housing components 112 of the test element 110, which all can be flexible housing components, may be combined by using a lamination process. Subsequently, an individualization of the test elements 110 may take place.

Embodiments

Embodiments include: A test element for detecting at least one analyte in a body fluid, the test element comprising: a housing having at least one base element and at least one cover element; at least one fluid channel formed within the housing, the fluid channel comprising at least two regions having differing depths, wherein the two regions comprise: a capillary region, and a measurement region, wherein the capillary region and the measurement region have differing aspect ratios; and at least one test field comprising at least one test chemical, the at least test field being part of the cover element, wherein the test chemical changes at least one optically measurable property in the presence of the at least one analyte, and wherein the cover element is mounted to the at least one base element by using the at least one adhesive, the at least one adhesive contacting the at least one test field in a manner that the adhesive is interposed in between the at least one test field and the at least one base element, wherein the at least one adhesive fully or partially covers the at least one test field such that the at least one adhesive is in direct contact with a test field surface or a part of the test field surface of the at least one test field.

In a further embodiment of the test element, the capillary region has a first depth, and wherein the measurement region has a second depth, the first depth being different from the second depth.

In a further embodiment of the test element, in between the capillary region and the measurement region, the at least one fluid channel further comprises a transition region.

In a further embodiment of the test element, the capillary region has an aspect ratio of 0.2 to 1.0.

In a further embodiment of the test element, the aspect ratio of the capillary region exceeds the aspect ratio of the measurement region by a factor of 2 to 20.

In a further embodiment of the test element, the fluid channel, in the capillary region, has a maximum width of 200 μm to 800 μm.

In a further embodiment of the test element, the at least one adhesive is a thermally activatable adhesive, the thermally activatable adhesive having a non-adhesive state, and wherein the thermally activatable adhesive is activatable by thermal activation, thereby bringing the thermally activatable adhesive in an adhesive state.

In a further embodiment of the test element, the at least one adhesive has hydrophilic properties, and in one aspect of this further embodiment the at least one adhesive at least partially covers the walls of the at least one fluid channel.

In a further embodiment of the test element, the at least one adhesive is selected from the group consisting of a polyethylene terephthalate foil, a polycarbonate foil, a polystyrene foil, a polyvinyl chloride foil, a polypropylene foil, a poly(methyl methacrylate), a polyurethane foil, and a polyester foil.

In a further embodiment of the test element, the cover element comprises a cover foil covering the capillary region and a test film comprising the at least one test field, and wherein the test film covers the measurement region.

In a further embodiment of the test element, the cover element is fully or partially coated by a hydrophilic coating.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

LISTING OF REFERENCE NUMBERS 110 test element
112 housing
114 base element
116 cover element
118 cover foil
120 test film
122 carrier foil
124 fluid channel
126 capillary region
128 transition region
130 measurement region
132 application position
134 adhesive
136 carrier foil
138 test field
140 test chemical
142 venting opening
144 abutting edge
146 surface
148 edge
150 longitudinal edge
152 bottom
154 wall
156 filling according to FIG. 4A
158 filling according to FIG. 4B
160 test element web
162 cutting line

The invention claimed is:

1. A method of manufacturing a test element for detecting at least one analyte in a body fluid, the method comprising the steps of:
providing at least one base element; and
mounting at least one cover element to the at least one base element by using at least one adhesive, wherein the at least one cover element comprises at least one test field having at least one test chemical, the at least one test chemical being adapted to change at least one optically measurable property in the presence of the analyte,
wherein the at least one adhesive contacts the at least one test field of the at least one cover element in a manner that the at least one adhesive is interposed in between the at least one test field and the at least one base element, wherein the at least one adhesive fully or partially covers the at least one test field such that the adhesive is in direct contact with a test field surface or a part of the test field surface of the at least one test field, and wherein the at least one base element and the at least one cover element form a housing of the test element, the test element further comprising at least one fluid channel formed within the housing, and wherein the at least one fluid channel is generally straight along its entirety and comprises a capillary region and a measurement region, the capillary region and the measurement region having differing aspect ratios, wherein the at least one fluid channel further comprises at least two sections having differing depths.

2. The method of claim 1, wherein the providing step further comprises the substeps of:
providing a carrier foil for the at least one base element; and
providing at least a part of the fluid channel within the carrier foil by using at least one forming process.

3. The method of claim 1, wherein the forming process is selected from the group consisting of a thermoforming process, a stamping, a thermal stamping, a punching, and an embossing.

4. The method of claim 1, wherein the at least one adhesive is a thermally activatable adhesive, the thermally activatable adhesive having a non-adhesive state, and wherein the thermally activatable adhesive is activatable by thermal activation, thereby bringing the thermally activatable adhesive in an adhesive state.

5. The method of claim 1, wherein the method comprises a reel-to-reel-process.

6. The method of claim 1, wherein the capillary region comprises a first depth and the measurement region comprises a second depth different from the first depth, the first depth being from about 50 μm to about 300 μm.

7. The method of claim 1, wherein the capillary region comprises a first depth and the measurement region comprises a second depth different from the first depth, the second depth being from about 20 μm to about 150 μm.

8. The method of claim 1, wherein the capillary region comprises a first depth and the measurement region comprises a second depth different from the first depth, and wherein the first depth exceeds the second depth by a factor of about 1.3 to about 3.

9. The method of claim 1, wherein the fluid channel in the capillary region has a maximum width of about 100 μm to about 1.0 mm.

10. The method of claim 1, wherein the fluid channel in the measurement region has a maximum width of about 500 μm to about 2.5 mm.

11. The method of claim 1, wherein the aspect ratio of the capillary region is defined by a maximum depth of the capillary region divided by a maximum width of the capillary region, and wherein said aspect ratio of the capillary region is from about 0.1 to about 1.5.

12. The method of claim 11, wherein said aspect ratio of the capillary region is from about 0.2 to about 1.0.

13. The method of claim 1, wherein the aspect ratio of the measurement region is defined by a maximum depth of the measurement region divided by a maximum width of the measurement region, and wherein the aspect ratio of the measurement region is from about 0.005 to about 0.2.

14. The method of claim 13, wherein the aspect ratio of the measurement region is from about 0.01 to about 0.1.

15. The method of claim 1, wherein the aspect ratio of the capillary region exceeds the aspect ratio of the measurement region by a factor of from about 2 to about 20.

16. The method of claim 15, wherein the factor is from about 5 to about 15.

17. The method of claim 15, wherein the factor is from about 9 to about 10.

18. The method of claim 1, wherein the aspect ratio of the capillary region is defined by a maximum depth of the capillary region divided by a maximum width of the capillary region, said aspect ratio of the capillary region being from about 0.1 to about 1.5, and wherein the aspect ratio of the measurement region is defined by a maximum depth of the measurement region divided by a maximum width of the measurement region, said aspect ratio of the measurement region being from about 0.005 to about 0.2.

19. The method of claim 18, wherein said aspect ratio of the capillary region is from about 0.2 to about 1.0, and wherein the aspect ratio of the measurement region is from about 0.01 to about 0.1.

* * * * *